US007709257B2

(12) United States Patent
Tew et al.

(10) Patent No.: US 7,709,257 B2
(45) Date of Patent: May 4, 2010

(54) MODELS FOR VACCINE ASSESSMENT

(75) Inventors: John G. Tew, Mechanicsville, VA (US); Mohey Eldin M. El Shikh, Richmond, VA (US); Inderpal Singh, Oviedo, FL (US); Eric Mishkin, Winter Springs, FL (US); Donald Drake, III, Orlando, FL (US); Haifeng Song, Ellicott City, MD (US); William L Warren, Orlando, FL (US)

(73) Assignees: Vax Design Corp., Orlando, FL (US); Virginia Commonwealth University, Richmond, VA (US)

( * ) Notice: Subject to any disclaimer, the term of this patent is extended or adjusted under 35 U.S.C. 154(b) by 26 days.

(21) Appl. No.: 11/819,335

(22) Filed: Jun. 27, 2007

(65) Prior Publication Data

US 2008/0008653 A1    Jan. 10, 2008

Related U.S. Application Data

(60) Provisional application No. 60/816,637, filed on Jun. 27, 2006.

(51) Int. Cl.
*C12N 5/00* (2006.01)
*C12N 5/02* (2006.01)
*C12N 5/16* (2006.01)

(52) U.S. Cl. .................... 435/373; 384/385; 384/347; 384/326

(58) Field of Classification Search ............... 435/373, 435/384, 385, 347, 326
See application file for complete search history.

(56) References Cited

U.S. PATENT DOCUMENTS

| | | | |
|---|---|---|---|
| 5,008,116 A | 4/1991 | Cahn | |
| 5,160,490 A | 11/1992 | Naughton et al. | |
| 5,354,686 A | 10/1994 | Haberman | |
| 5,562,910 A | 10/1996 | Daynes et al. | |
| 5,725,856 A | 3/1998 | Hudziak et al. | |
| 5,739,001 A | 4/1998 | Brown et al. | |
| 5,750,329 A | 5/1998 | Quinn et al. | |
| 6,177,282 B1 | 1/2001 | McIntyre | |
| 6,274,378 B1 | 8/2001 | Steinman et al. | |
| 6,479,064 B1 | 11/2002 | Atala | |
| 6,835,550 B1 | 12/2004 | Estell et al. | |
| 2002/0155108 A1 | 10/2002 | Barbera-Guillem et al. | |
| 2003/0109042 A1 | 6/2003 | Wu et al. | |
| 2003/0147923 A1 | 8/2003 | Klaviniskis | |
| 2003/0199006 A1 | 10/2003 | Britz et al. | |
| 2003/0207287 A1 | 11/2003 | Short | |
| 2004/0009943 A1 | 1/2004 | Semple et al. | |
| 2004/0109876 A1 | 6/2004 | Yamamoto et al. | |
| 2004/0234510 A1 | 11/2004 | Mochitate | |
| 2005/0191743 A1 | 9/2005 | Wu et al. | |
| 2005/0229264 A1 | 10/2005 | Chang et al. | |
| 2005/0282148 A1 | 12/2005 | Warren et al. | |
| 2006/0105454 A1 | 5/2006 | Son et al. .................... 435/325 |
| 2006/0270029 A1 | 11/2006 | Warren et al. | |
| 2006/0275270 A1 | 12/2006 | Warren et al. | |
| 2007/0015136 A1 | 1/2007 | Sanchez-Schmitz et al. | |
| 2007/0141552 A1 | 6/2007 | Warren et al. | |
| 2007/0154956 A1 | 7/2007 | Warren et al. | |
| 2007/0178076 A1 | 8/2007 | Drake et al. | |
| 2007/0218054 A1 | 9/2007 | Sukumar et al. | |
| 2008/0008653 A1 | 1/2008 | Tew et al. | |

FOREIGN PATENT DOCUMENTS

| | | |
|---|---|---|
| EP | 0358506 | 9/1989 |
| EP | 1437147 | 9/2002 |
| EP | 1970444 | 12/2006 |
| WO | WO 99/15629 | 4/1999 |
| WO | WO 99/43788 | 9/1999 |
| WO | WO 99/49319 | 9/1999 |
| WO | WO 03/041568 | 5/2003 |
| WO | WO 03/050271 | 6/2003 |
| WO | WO 2004/031361 | 4/2004 |
| WO | WO 2004/101773 | 11/2004 |
| WO | WO 2005/104755 | 11/2005 |
| WO | WO 2007/075979 | 7/2007 |
| WO | WO 2007/106559 | 9/2007 |
| WO | WO 2007/146267 | 12/2007 |

OTHER PUBLICATIONS

Boni, A et al., 2006, Prolonged exposure of dendritic cells to maturation stimuli favors the induction of type-2 cytotoxic T lymphocytes, Eur. J. Immunol., 36:3157-3166.*
Caux, C et al., 1995, Human dendritic langerhans cells generated in vitro from CD34+ progenitors can prime naïve CD4+ T cells and process soluble antigen, Jour Immunol, 155:5427-5435.*
Moser, M et al, 2000, Dendritic cell regulation of TH1-TH2 development, Nature Immunology, 1:199-205.*
Ansel, et al., "A Chemokine-Driven Positive Feedback Loop Organizes Lymphoid Follicles", Nature, vol. 406, pp. 309-314 (2000).
Aydar et al. (2005) *J. Immunol.* 174, 5358-5366.
Badylak, S.F. et al., "Small Intestinal Submucosa: A Substrate for in vitro Cell Growth," J. Biomater. Sci. Polymer Edn. (1998), vol. 9, No. 8, pp. 863-878.

(Continued)

*Primary Examiner*—Valarie Bertoglio
(74) *Attorney, Agent, or Firm*—Roylance, Abrams

(57) ABSTRACT

The present invention is directed to methods for constructing and using in vivo and in vitro models of aspects of human immunity and, in particular, construction of a human immune system model for the testing of, for example, vaccines, adjuvants, immunotherapy candidates, cosmetics, drugs, biologics and other chemicals. The present invention comprises both in vivo and in vitro models of aspects of human immunity that are useful for assessing the interaction of substances with the immune system, and thus can be used to accelerate and improve the accuracy and predictability of, for example, vaccine, drug, biologic, immunotherapy, cosmetic and chemical development. The invention is also useful for the generation of human monoclonal and polyclonal antibodies.

6 Claims, 27 Drawing Sheets

OTHER PUBLICATIONS

Bai et al., "*Generation of Dendritic Cells From Human Bone Marrow Mononuclear Cells: Advantages From Clinical Applications in Comparison to Peripheral Blood Monocyte Derived Cells*," International Journal of Oncology, (2002), 20(2), pp. 247-253.

Banchereau, et al., "Dendritic Cells and the Control of Immunity", Nature, vol. 392, pp. 245-252 (1998).

Banchereau, et al., "Immunobiology of Dendritic Cells", Annu. Rev. Immunol., vol. 18, pp. 767-811 (2000).

Baumgarth, "A Two-Phase Model of B-Cell Activation", Immunological Review, vol. 176, pp. 171-180 (2000).

Benbrook et al., "Organotypic cultures represent tumor microenvironment for drug testing," Drug Discovery Today: Disease Models, 3(2), pp. 143-148 (2005).

Berman, et al., "Roles of Platelet/Endothelial Cell Adhesion Molecule-1 (PECAM-1, CD31) in Natural Killer Cell Transendothelial Migration and Beta 2 Integrin Activation", The Journal of Immunology, vol. 156, pp. 1515-1524 (1996).

Birkness et al., A Tissue Culture Bilayer Model to Study the Passage of *Neisseria meningitidis*, Infection and Immunity, Feb. 1995, p. 402-409, vol. 63, No. 2.

Birkness et al., An In Vitro Tissue Culture Bilayer Model to Examine Early Events in *Mycobacterium tuberculosis* Infection, Infection and Immunity, Feb. 1999, p. 653-658, vol. 67, No. 2.

Bogdan, et al., "Fibroblasts as Host Cells in Latent Leishmaniosis", J. Exp. Med., vol. 191, pp. 2121-2129 (2000).

Boni et al. (2006) Eur. J. Immunol. 36, 3157-3166.

Brandtzaeg, P. et al., "*Mucosal B Cells: Phenotypic Characteristics, Transcriptional, Regulation, and Homing Properties*," Immunological Reviews (2005), vol. 206, pp. 32-63.

Bromelow, K. V. et al., "*Whole Blood Assay for Assessment of the Mixed Lymphocyte Reaction*," Journal of Immunological Methods, (2001), 247(1-2), pp. 1-8.

Büchele, S. et al., "*Presentation of Tetanus Toxoid to Autologous T Cells by Dendritic Cells Generated From Human Blood. Improved Specificity With Dendritic Cells Generated Without Fetal Calf Serum*," Advances in Experimental Medicine and Biology, (1997), vol. 417, pp. 233-237.

Buchler et al. (2003) Vaccine, 21, 877-882.

Butcher, et al., "Lymphocyte Trafficking and Regional Immunity", Advances in Immunology, vol. 72, pp. 209-253 (1999).

Castro, et al., "Spleen-Derived Stromal Cells. Adhesion Molecules Expression and Lymphocyte Adhesion to Reticular Cells", Eur. J. Cell. Biol., vol. 74, 321-328 (1997).

Caux et al. (1995) J. Immunol. 155, 5427-5435.

Cayeux et al. (1999) Eur. J. Immunol. 29, 225-234.

Chen, et al., "A Film Tension Theory of Phagocytosis", Journal of Colloid and Interface Science, vol. 190, pp. 118-133 (1997).

Chou, et al., "The Detection of the HLA-B27 Antigen by Immunomagnetic Separation and Enzyme-Linked Immunosorbent Assay-Comparison with a Flow Cytometric Procedure", Journal of Immunological Methods, vol. 255, pp. 15-22 (2001).

Crivellato, et al., "Stromal Cell Organisation in the Mouse Lymph Node. A Light and Electron Microscopic Investigation Using the Zinc Iodide-Osmium Technique", J. Anat., vol. 190, pp. 85-92 (1997).

Cyster, "Chemokines and the Homing of Dendritic Cells to the T Cell Areas of Lymphoid Organs", J. Exp. Med. vol. 189, No. 3, pp. 447-450 (1999).

Cyster, et al., "Follicular Stromal Cells and Lymphocyte Homing to Follicles", Immunological Reviews, vol. 176, pp. 181-193 (2000).

Danke, et al., "HLA Class II-Restricted CD4+ T Cell Responses Directed Against Influenza Viral Antigens Postinfluenza Vaccination", The Journal of Immunology, vol. 171, pp. 3163-3169 (2003).

Denkbas, et al., "Magnetic Chotosan Microspheres: Preparation and Characterization", Reactive & Functional Polymers, vol. 50, pp. 225-232 (2002).

Dubey et al. (2005) J. Clin. Endocrin & Met., 90, 247-255.

Dubois, et al., "Dendritic Cells Enhance Growth and Differentiation of CD40-Activated B Lymphocytes", J. Exp. Med., vol. 185, pp. 941-951 (1997).

Edelman et al, A Cultureal Renaissance: In Vitro Cell Biology Embraces Three-Dimensional Context. Exp Neurol. 2005, vol. 192, pp. 1-6.

El Shikh, M. et al., "*Follicular Dendritic Cells Stimulated by Collagen Type I Develop Dendrites and Networks In Vitro*," Cell and Tissue Research, (2007), 329(1), pp. 81-89.

Forster, et al., "CCR7 Coordinates the Primary Immune Response by Establishing Functional Microenvironments in Secondary Lymphoid Organs", Cell., vol. 99, pp. 23-33 (1999).

Fransson, et al., "Culture of Human Epidermal Langerhans Cells in a Skin Equivalent", British Journal of Dermatology, vol. 139, pp. 598-604 (1998).

Friedl, et al., "CD4+ T Lymphocytes Migrating in Three-Dimensional Collagen Lattices Lack Focal Adhesions and Utilize Beta 1 Integrin-Independent Strategies for Polarization, Interaction with Collagen Fibers and Locomotion", Eur. J. Immunol., vol. 28, pp. 2331-2343 (1998).

Fulcher, et al., "B-Cell Activation Versus Tolerance—The Central Role of Immunoglobulin Receptor Engagement and T-Cell Help", Int. Rev. Immunol., vol. 15, pp. 33-52 (1997).

Furie, et al., "Migration of Neutrophils Across Endothelial Monolayers is Stimulated by Treatment of the Monolayers with Interleukin-1 or Tumor Necrosis Factor-Alpha", The Journal of Immunology, vol. 143, pp. 3309-3317 (1989).

Furuyama, A. et al., "*Assembly of Basement Membrane in vitro by Cooperation Between Alveolar Epithelial Cells and Pulmonary Fibroblasts*," Cell Structure and Function (1997), vol. 22, pp. 603-614.

Galibert, et al., "CD40 and B Cell Antigen Receptor Dual Triggering of Resting B Lymphocytes Turns on a Partial Germinal Center Phenotype", J. Exp. Med., vol. 183, pp. 77-85 (1996).

Garside, et al., "Visualization of Specific B and T Lumphocyte Interactions in the Lymph Node", Science, vol. 281, pp. 96-99 (1998).

Gergel, et al., "Activation of Endothelium by *Borrelia burgdorferi* In Vitro Enhances Transmigration of Specific Subsets of T Lymphocytes", Infection and Immunity, vol. 69, pp. 2190-2197 (2001).

Gretz, et al., "Cords, Channels, Corridors and Conduits: Critical Architectural Elements Facilitating Cell Interactions in the Lymph Node Cortex", Immunological Reviews, vol. 156, pp. 11-24 (1997).

Gretz, et al., "Lymph-borne Chemokines and Other Low Molecular Weight Molecules Reach High Endothelial Venules Via Specialized Conduits While a Functional Barrier Limits Access to the Lymphocyte Microenvironments in Lymph Node Cortex", The Journal of Experimental Medicine, vol. 192, pp. 1425-1439 (2000).

Gretz, et al., "Sophisticated Strategies for Information Encounter in the Lymph Node: The Reticular Network as a Conduit of Soluble Information and a Highway for Cell Traffic", The Journal of Immunology, vol. 157, pp. 495-499 (1996).

Gundersen, et al., "Magnetic Bead Antigen Capture Enzyme-Linked Immunoassay in Microtitre Trays for Rapid Detection of Schistosomal Circulating Anodic Antigen", Journal of Immunological Methods, vol. 148, pp. 1-8 (1992).

Gunn, et al., "Mice Lacking Expression of Secondary Lymphoid Organ Chemokine Have Defects in Lymphocyte Homing and Dentritic Cell Localization", J. Exp. Med., vol. 189, pp. 451-460 (1999).

Gunzer, et al., "Antigen Presentation in Extracellular Matrix: Interactions of T Cells with Dendritic Cells are Dynamic, Short Lived, and Sequential", Immunity, vol. 13, pp. 323-332 (2000).

Hasbold, et al., "Quantitative Analysis of Lymphocyte Differentiation and Proliferation in Vitro Using CarboxyFluorescein Diacetate Succinimidyl Ester", Immunology and Cell Biology, vol. 77, pp. 516-522 (1999).

Irvine, et al., "Nanoscale Clustering of RGD Peptides at Surfaces Using Comb Polymers. 1. Synthesis and Characterization of Comb Thin Films", Biomacromolecules, vol. 2, pp. 85-94 (2001).

Jenkins, et al., "In Vivo Activation of Antigen-Specific CD4 T Cells", Annu. Rev. Immunol., vol. 19, pp. 23-45 (2001).

Junt, et al., "Antiviral Immune Responses in the Absence of Organized Lymphoid T Cell Zones in *plt/plt* Mice", The Journal of Immunology, vol. 168, pp. 6032-6040 (2002).

Kabashima, et al., "Prostaglandin E$_2$-EP4 Signaling Initiates Skin Immune Responses by Promoting Migration and Maturation of Langerhans Cells", Nature Medicine, vol. 9, pp. 744-749 (2003).

Kadowaki, et al., "Subsets of Human Dendritic Cell Precursors Express Different Toll-Like Receptors and Respond to Different Microbial Antigens", J. Exp. Med. vol. 194, No. 6, pp. 863-869 (2001).

Kaldjian, et al., "Spatial and Molecular Organization of Lymph Node T Cell Cortex: A Labyrinthine Cavity Bounded by an Epithelium-Like Monolayer of Fibroblastic Reticular Cells Anchored to Basement Membrane-like Extracellular Matrix", International Immunology, vol. 13, pp. 1243-1253 (2001).

Khademhosseini et al., "*Microscale Technologies for Tissue Engineering and Biology*," Proc. Natl. Acad. Sci. USA, vol. 103, pp. 2480-2487 (2006).

Kim et al., "*Three-Dimensional Tissue Culture Models in Cancer Biology*," Seminars in Cancer Biology, (2005), 15(5), pp. 365-377.

Kim, H.-J. et al, Establishment of Early Lymphoid Organ Infrastructure in Transplanted Tumors Mediated by Local Production of Lymphotoxin α and in Combined Absence of Functional B and T Cells. In J. of Immunology, vol. 172:4037-4047 (2004).

Kosco, M. H. et al., "*Folicular Dendritic Cell-Dependent B-Cell Proliferation and In Vitro Germinal Center*," Lymphatic Tissues In Vivo Immune Responses, (1991), pp. 687-690.

Kosco, M. H. et al., "*Follicular Dendritic Cell-Dependent Adhesion and Proliferation of B Cells In Vitro*," Journal of Immunology, (1992), 148(8), pp. 2331-2339.

Kosco, M. H. et al., "*Follicular Dendritic Cells and Germinal Center Formation In-Vitro*," Accessory Cells in HIV and Other Retroviral Infections: Morphological and Functional Aspects; Workshop on Morphological and Functional Aspects of Accessory Cells in retroviral Infections, Hamberg, Germany, 23-24, p. 44-49 (1991).

Kosco-Vilbois, "Are Follicular Dendritic Cells Really Good for Nothing", Nature Reviews Immunology, vol. 3, pp. 764-769 (2003).

Kourilov, et al., "Magnetic-Bead Enzyme-Linked Immunosorbent Assay Verifies Adsorption of Ligand and Epitope Accessibility", Analytical Biochemistry, vol. 311, pp. 166-170 (2002).

Larsson, et al., "Requirement of Mature Dendritic Cells for Efficient Activation of Influenza A-Specific Memory CD8 + T Cells", The Journal of Immunology, vol. 165, pp. 1182-1190 (2000).

LeBedis, et al., "Peripheral Lymph Node Stromal Cells Can Promote Growth and Tumorigenicity of Breast Carcinoma Cells Through the Release of IGF-I and EGF", Int. J. Cancer, vol. 100, pp. 2-8 (2002).

Levenberg, S. et al., "*Advances in Tissue Engineering*," Current Topics in Developmental Biology, (2004), vol. 61, pp. 113-134.

Luk, et al., "Rapid and Sensitive Detection of *Salmonella* (O:6,7) by Immunomagnetic Monoclonal Antibody-Based Assays", Journal of Immunological Methods, vol. 137, pp. 1-8 (1991).

Lukas, et al., "Human Cutaneous Dendritic Cells Migrate Through Dermal Lymphatic Vessels in a Skin Organ Culture Model", The Journal of Investigative Dermatology, vol. 106, pp. 1293-1299 (1996).

Manna, P. et al., "Differentiation and Functional Maturation of Human CD14<+> Adherent Peripheral Blood Monocytes by Xenogeneic Endothelial Cells: Up-Regulation of Costimulation Cytokine Generation, and Toll-Like Receptors," Transplantation, (2002), 74(2), pp. 243-252.

Matsumoto, et al., "Affinity Maturation Without Germinal Centres in Lymphotoxin-α-Deficient Mice", Nature, vol. 382, pp. 462-466 (1996).

Mebius, "Organogenesis of Lymphoid Tissues", Nat. Rev. Immunol, vol. 3, pp. 292-303 (2003).

Mellman, et al., "Dendritic Cells: Specialized and Regulated Antigen Processing Machines", Cell, vol. 106, pp. 255-258 (2001).

Miller, et al., "Two-Photon Imaging of Lymphocyte Motility and Antigen Response in Intact Lymph Node", Science, vol. 296, pp. 1869-1873 (2002).

Mori, et al., "Mice Lacking Expression of the Chemokines CCL21-ser and CCL19 (plt Mice) Demonstrate Delayed but Enhanced T Cell Immune Responses", J. Exp. Med., vol. 193, No. 2, pp. 207-217 (2001).

Moser et al. (2000) *Nature Immunol.* 1, 199-205.

Nakamura, M. et al., "*Expression of Leptin in Two-layered Culture of Gastric Mucous Cells and Fibroblasts: Effect of Helicobacter pylori Attachment*," Aliment Pharmacol Ther. (2004), vol. 20, suppl. 1, pp. 125-130.

Nakatsu, M. N. et al., "*Angiogenic Sprouting and Capillary Lumen Formation Modeled by Human Umbilical Vein Endothelial Cells (HUVEC) in Fibrin Gels: The Role of Fibroblasts and Angiopoietin-I*," Microvascular Research (2003), vol. 66, pp. 102-112.

Neves, A. R. et al., "*Dendritic Cells Derived From Metastatic Cancer Vaccinated With Allogeneic Dendritic Cell-Autologous Tumor Cell Hybrids Express More CD86 and Induce Higher Levels of Interferon-Gamma in Mixed Lymphocyte Reactions*," Cancer Immunology and Immunotherapy, (2005), 54(1), pp. 61-66.

Oehler et al. (2000) *Ann. Hematol.*, 79, 355-362.

Okamoto et al, Artificial Lymph Nodes Induce Potent Secondary Immune Response in Naïve and Immunodeficient Mice. J. Clin. Invest. Apr. 2007, vol. 117, No. 4, pp. 997-1007.

Parker, "T Cell-Dependent B Cell Activation", Annu. Rev. Immunol., vol. 11, pp. 331-360 (1993).

Pasparakis, et al., "Immune and Inflammatory Responses in TNFα Deficient Mice: A Critical Requirement for TNFα in the Formation of Primary B Cell Follicles, Follicular Dendritic Cell Networks and Germinal Centers, and in the Maturation of the Humoral Immune Response", J. Exp. Med., vol. 184, pp. 1397-1411 (1996).

Phillips, et al., "Activation of Pertussis Toxin-Sensitive CXCL12 (SDF-1) Receptors Mediates Transendothelial Migration of T Lymphocytes Across Lymph Node High Endothelial Cells", Eur. J. Immunol., vol. 32, pp. 837-847 (2002).

Podgrabinska, et al., "Molecular Characterization of Lymphatic Endothelial Cells", Proc. Natl. Acad. Sci. U.S.A., vol. 99, No. 25, pp. 16069-16074 (2002).

Portner, R et al, Chapter 2: An Overview on Bioreactor Design, Prototyping, and Process Control for Reproducible Three-Dimensional Tissue Culture. In Drug Testing In Vitro: Breakthrough Cell Cultur Technology. Eds. U. Marx and V. Sandig 2006: Wiley-VCH, pp. 65-69.

Poznansky, et al., "Efficient Generation of Human T Cells From a Tissue-Engineered Thymic Organoid", Nature Biotechnology, vol. 18, pp. 729-734 (2000).

Qu, et al., "Autocrine Type I IFN and Contact with Endothelium Promote the Presentation of Influenza A Virus by Monocyte-Derived APC", The Journal of Immunology, vol. 170, pp. 1010-1018 (2003).

Randolph, et al., "A Physiologic Function for p-Glycoprotein (MDR-1) During the Migration of Dendritic Cells from Skin Via Afferent Lymphatic Vessels", Proc. Natl. Acad. Sci., vol. 95, pp. 6924-2929 (1998).

Randolph, et al., "A Soluble Gradient of Endogenous Monocyte Chemoattractant Protein-1 Promotes the Transendothelial Migration of Monocytes In Vitro", The Journal of Immunology, vol. 155, pp. 3610-3618 (1995).

Randolph, et al., "Differentiation of Monocytes into Dendritic Cells in a Model of Transendothelial Trafficking", Science, vol. 282, pp. 480-483 (1998).

Randolph, et al., "Mononuclear Phagocytes Egress from an In Vitro Model of the Vascular Wall by Migrating Across Endothelium in the Basal to Apical Direction: Role of Intercellular Adhesion Molecule 1 and the CD11/CD18 Integrins", J. Exp. Med., vol. 183, pp. 451-462 (1996).

Randolph, et al., "Role of Tissue Factor in Adhesion of Mononuclear Phagocytes to and Trafficking Through Endothelium in Vitro", Blood, vol. 92, pp. 4167-4177 (1998).

Randolph, et al., "The CD16(+) (FcγRIII(+)) Subset of Human Monocytes Preferentially Becomes Migratory Dendritic Cells in a Model Tissue Setting", J. Exp. Med., vol. 196, No. 4, pp. 517-527 (2002).

Razanajaona, et al., In Vitro Triggering of Somatic Mutation in Human Naïve B Cells, The Journal of Immunology, vol. 159, pp. 3347-3353 (1997).

Regnier, et al., "Integration of Langerhans Cells into a Pigmented Reconstructed Human Epidermis", The Journal of Investigative Dermatology, vol. 109, No. 4, pp. 510-512 (1997).

Robbiani, et al., "The Leukotriene C4 Transporter MRP1 Regulates CCL19 (MIP-3β, ELC)-Dependent Mobilization of Dendritic Cells to Lymph Nodes", Cell, vol. 103, pp. 757-768 (2000).

Roos et al. (2005) *Expert Opin. Drug Metab. Toxicol.* 1, 187-202.

Rot, "In Situ Binding Assay for Studying Chemokine Interactions with Endothelial Cells", Journal of Immunological Methods, vol. 273, pp. 63-71 (2003).

Ruco, et al., "Expression and Cell Distribution of the Intercellular Adhesion Molecule, Vascular Cell Adhesion Molecule, Endothelial Leukocyte Adhesion Molecule, and Endothelial Cell Adhesion Molecule (CD31) in Reactive Human Lymph Nodes and in Hodgkin's Disease", American Journal of Pathology, vol. 140, pp. 1337-1344 (1992).

Safarik, et al., "Use of Magnetic Techniques for the Isolation of Cells", Journal of Chromatography B, vol. 722, pp. 33-53 (1999).

Santini et al. (2000) *J. Exp. Med.* 191, 1777-1788.

Sarradell et al. (2003) *Vet. Pathol.*, 40, 395-404.

Seguin, R. et al., "*Human Brain Endothelial Cells Supply Support for Monocyte Immunoregulartory Functions,*" Journal of Neuroimmunology, (2003), 135(1-2), pp. 96-106.

Sieben, et al., "Comparison of Different Particles and Methods for Magnetic Isolation of Circulating Tumor Cells", Journal of Magnetism and Magnetic Materials, vol. 225, pp. 175-179 (2001).

Skibinski, et al., "Enhancement of Terminal B Lymphocyte Differentiation in Vitro by Fibroblast-Like Stromal Cells from Human Spleen", Eur. J. Immunol., vol. 28, pp. 3940-3948 (1998).

Skibinski, et al., "The Role of Hepatocyte Growth Factor and Its Receptor *c-met* in Interactions Between Lymphocytes and Stromal Cells in Secondary Human Lymphoid Organs", Immunology, vol. 102, pp. 506-514 (2001).

Soderberg, O. et al., "*The Human Follicular Dendritic Cell Line FDC-1 Binds Immune Complexes and Promotes Somatic Hypermutation,*" Blood, (2001), 98(11 part 2), pp. 40b.

Sprent, et al., "Antigen-Induced Selective Recruitment of Circulating Lymphocytes", Cellular Immunology, vol. 2, pp. 171-181 (1971).

Stoll, et al., "Dynamic Imaging of T Cell-Dendritic Cell Interactions in Lymph Nodes", Science, vol. 296, pp. 1873-1876 (2002).

Stuart, et al., "The Human Reticular Cell: Morphology and Cytochemistry", J. Pathol, vol. 103, pp. 41-47 (1971).

Suematsu, et al., "Generation of a Synthetic Lymphoid Tissue-Like Organoid in Mice", Nature Biotechnology, vol. 22, No. 12, pp. 1539-1545 (Dec. 2004).

Tan et al. (2005) *J. Leuk. Biol.* 78, 319-324.

Tarte et al., Leukemia, vol. 14, 2000, abstract p. 2182.

Tew et al. (2001) *Trends Immunol.* 22, 361-367.

Tew, J. G. et al., "*Follicular Dendritic Cells As Accessory Cells,*" Immunological Reviews, (1990), No. 117, pp. 185-211.

Tew, J.G. et al., "*Follicular Dendritic Cells and Presentation of Antigen and Costimulatory Signals to B Cells,*" Immunological Reviews (1997), vol. 156, pp. 39-52.

Thompson, H.G. et al., "*A Three-dimensional in vitro Model of Angiogenesis in the Airway Mucosa,*" Pulmonary Pharmacology & Therapeutics (2007), vol. 20, pp. 141-148.

Toyama, et al., "Memory B Cells Without Somatic Hypermutation are Generated from Bcl 6 Deficient B Cells", Immunity, vol. 17, pp. 329-339 (2002).

Tsunoda, R. et al., "*Follicular Dendritic Cells In Vitro Modulate the Expression of Fas and Bcl-2 on Germinal Center B Cells,*" Cell and Tissue Research, (2000), 299(3), pp. 395-402.

Tsunoda, R. et al., "*Human Follicular Dendritic Cells In Vitro and Follicular Dendritic-Cell-Like Cells,*" Cell and Tissue Research, (1997), 288(2), pp. 381-389.

Van Den Berg, et al., "Localization of β 1 Integrins and Their Extracellular Ligands in Human Lymphoid Tissues", American Journal of Pathology, vol. 143, pp. 1098-1110 (1993).

Weppler et al., Modulation of Endotoxin-Induced Neutrophil Transendothelial Migration by Alveolar Epithelium in a Defined Bilayer Model, *Experimental Lung Research* 32:10, 455-482 (2006).

West, et al., "Polymeric Biomaterials with Degradation Sites for Proteases Involved in Cell Migration", Macromolecules, vol. 32, pp. 241-244 (1999).

Wu et al. (2008) *J. Immunol.* 180, 281-290.

Wu, Y. et al., "*Influence of Follicular Dendritic Cells and Primed T Cells on Somatic Hypermutation in In Vitro Germinal Centers,*" Journal of Immunology, (2006), 176(suppl. S), pp. S235-S236.

Zhang, S. et al., "*Growth Factors Secreted by Bronchial Epithelial Cells Control Myofibroblast Proliferation: An in vitro Co-culture Model of Airway Remodeling in Asthma,*" Laboratory Investigation (1999), vol. 79, No. 4, pp. 395-405.

International Search Report—PCT/US2007/083795.
International Search Report—PCT/US2008/056720.
International Search Report—PCT/US08/70107a.
International Search Report—PCT/US06/048959.
International Search Report—PCT/US07/014826.
International Search Report—PCT/US08/69172.
International Search Report—PCT/US07/013745.
International Search Report—PCT/US05/14444.
International Search Report—PCT/US06/43563.
International Search Report—PCT/US06/43712.
International Search Report—PCT/US07/006532.
International Search Report—PCT/US07/006571.
International Search Report—PCT/US07/013871.
International Search Report—PCT/US06/049128.
International Search Report—PCT/US08/70107b.

Dynal (Norway): http://www.invitrogen.com/.
Agowa GMBH (Germany): http://agowade/contentsframes/magneticseparation/particle.html.
http://www.xcyte.com.
Protocol for anti-CD3 Activation of T-Cells from E-Bioscience (San Diego, CA): http://www.ebioscience..com/ebioscience/appls/AC145.htm.

U.S. Appl. No. 11/116,234, filed Apr. 28, 2005, Pending.
U.S. Appl. No. 11/375,033, filed Mar. 15, 2006, Pending.
U.S. Appl. No. 11/375,128, filed Mar. 15, 2006, Abandoned.
U.S. Appl. No. 11/471,514, filed Jun. 21, 2006, Pending.
U.S. Appl. No. 11/453,046, filed Jun. 15, 2006, Pending.
U.S. Appl. No. 11/453,003, filed Jun. 15, 2006, Pending.
U.S. Appl. No. 11/594,171, filed Nov. 8, 2006, Abandoned.
U.S. Appl. No. 11/594,172, filed Nov. 8, 2006, Pending.
U.S. Appl. No. 12/047,107, filed Mar. 12, 2008, Pending.
U.S. Appl. No. 11/642,938, filed Dec. 12, 2006, Pending.
U.S. Appl. No. 11/642,926, filed Dec. 12, 2006, Pending.
U.S. Appl. No. 11/819,335, filed Jun. 27, 2007, Pending.
U.S. Appl. No. 12/167,689, filed Jul. 3, 2008, Pending.
U.S. Appl. No. 12/173,921, filed Jul. 16, 2008, Pending.

D'Amico et al., *Blood* 92:207-214 (1998).
Simmingskoeld et al., *Scand. J. Immunol.* 7:233-238 (1978).
Transwell® Permeable Supports Selection and Use Guide, Corning Corp., pp. 1-12 (2009).
Dubois et al., J. Leukocyte Biology, 1999, v.66, p. 224-230.
Gansuvd et al., Human Immunol., 2003, v.64, p. 427-439.
Clayton et al., Clin. Exp. Immunol., 2003, v.132, p. 174-179.

* cited by examiner

Follicular Dendritic Cells (FDCs)

- Cardinal features of FDCs

1. Located in the follicles of secondary lymphoid tissue.

2. Dendritic morphology -- Note the numerous processes wrapped "spaghetti-like" and the beads (Iccosomes) on scanning electron micrograph of the FDC.

3. Binds and retains immune complexes (ICs).

Note the Ab response (anti-OVA production) when FDCs are added to the memory lymphocytes (Ly) plus ICs over a dose range.

A.

B.

MODELS FOR VACCINE ASSESSMENT

CROSS-REFERENCE TO RELATED APPLICATIONS

This application claims priority from U.S. Provisional Appl. No. 60/816,637, filed Jun. 27, 2006, which is incorporated by reference herein in its entirety for all purposes.

FIELD OF THE INVENTION

The present invention is directed to a method for constructing models of aspects of human immunity and, in particular, construction of a human immune system model for testing of vaccines, adjuvants, immunotherapy candidates, cosmetics, drugs, biologics, and other chemicals.

BACKGROUND OF THE TECHNOLOGY

Despite the advent and promise of recent technologies, including combinatorial chemistry, high-throughput screening, genomics, and proteomics, the number of new drugs and vaccines reaching the market has not increased. In fact, the attrition rate within drug discovery programs still exceeds 90%.

The introduction of these new (and expensive) technologies has not reduced the lost opportunity costs associated with immunotherapy development; rather, these costs have increased. Indeed, it is now estimated that almost $1 billion is required to bring a new drug to the market.

The development and biological testing of human vaccines has traditionally relied on small animal models (e.g., mouse and rabbit models) and then non-human primate models. However, such small animal models are expensive and non-human primate models are both expensive and precious. Furthermore, there are many issues regarding the value of such animal studies in predicting outcomes in human studies.

A major problem remains the translation from test systems to human immunology. Successful transfer between traditional testing systems and human biology requires an intricate understanding of disease pathogenesis and immunological responses at all levels. Given worldwide health problems caused by known and emerging infectious agents and even potential biological warfare pathogens, it is time for a fresh approach to understanding disease pathogenesis, the development and rapid testing of vaccines, and insights gathered from such work.

The body's distributed immune system can be roughly divided into four distinct compartments: tissues and blood, mucosal tissues, body cavities, and skin. Because of ease of study, most is known about the tissue and blood compartment and its lymphoid tissues, the spleen and lymph nodes.

The mammalian immune system uses two general mechanisms to protect the body against environmental pathogens. The immune system recognizes and responds to structural differences between self and non-self proteins. Proteins that the immune system recognizes as non-self are referred to as antigens. Pathogens typically express large numbers of complex antigens. When a pathogen-derived molecule is encountered, the immune response becomes activated to enable protection against that pathogenic organism.

The first immune system mechanism is the non-specific (or innate) inflammatory response. The innate immune system appears to recognize specific molecules that are present on pathogens but not on the body itself.

The second immune system mechanism is the specific or acquired (or adaptive) immune response; acquired immunity is mediated by specialized immune cells called B and T lymphocytes (or simply B and T cells). Acquired immunity has specific memory for antigenic structures; repeated exposure to the same antigen increases the response, which increases the level of induced protection against that particular pathogen. Whereas innate responses are fundamentally the same for each injury or infection, acquired responses are custom-tailored to the pathogen in question. The acquired immune system evolves a specific immunoglobulin (antibody) response to many different molecules present in the pathogen, called antigens. In addition, a large repertoire of T cell receptors (TCR) is sampled for their ability to bind processed forms of the antigens bound to major histocompatibility complex (MHC, also known as human leukocyte antigen, HLA) class I and II proteins on the surface of antigen-presenting cells (APCs), such as dendritic cells (DCs).

B cells produce and mediate their functions through the actions of antibodies. B cell-dependent immune responses are referred to as "humoral immunity," because antibodies are found in body fluids.

T cell-dependent immune responses are referred to as "cell-mediated immunity," because effector activities are mediated directly by the local actions of effector T cells. The local actions of effector T cells are amplified through synergistic interactions between T cells and secondary effector cells, such as activated macrophages. The result is that the pathogen is killed and prevented from causing diseases.

The functional element of mammalian secondary lymphoid tissues, including lymph nodes, is the follicle, which develops a germinal center (GC) when stimulated by an antigen. The GC is an active area within a lymph node, where important interactions occur in the development of an effective humoral immune response. Upon antigen stimulation, follicles are replicated and an active human lymph node may have dozens of active follicles, with functioning GCs. Interactions between B cells, T cells, and FDCs take place in GCs.

Various studies of GCs in vivo indicate that the many important events occur there, including immunoglobulin (Ig) class switching, rapid B cell proliferation (GC dark zone), production of B memory cells, accumulation of select populations of antigen-specific T cells and B cells, hypermutation, selection of somatically mutated B cells with high affinity receptors, apoptosis of low affinity B cells, affinity maturation, induction of secondary antibody responses, and regulation of serum immunoglobulin G (IgG) with high affinity antibodies. Similarly, data from in vitro GC models indicate that FDCs are involved in stimulating B cell proliferation with mitogens and it can also be demonstrated with antigen (Ag), promoting production of antibodies including recall antibody responses, producing chemokines that attract B cells and certain populations of T cells, immunoglobulin class switching, somatic hypermutation, selection of high affinity B cells, promoting production of high affinity antibodies, and blocking apoptosis of B cells.

Similar to pathogens, vaccines function by initiating an innate immune response at the vaccination site and activating antigen-specific T and B cells that can give rise to long term memory cells in secondary lymphoid tissues. The precise interactions of the vaccine with cells at the vaccination site and with T and B cells of the lymphoid tissues are important to the ultimate success of the vaccine.

Almost all vaccines to infectious organisms were and continue to be developed through the classical approach of generating an attenuated or inactivated pathogen as the vaccine itself. This approach, however, fails to take advantage of the recent explosion in our mechanistic understanding of immunity. Rather, it remains an empirical approach that consists of making variants of the pathogen and testing them for efficacy in non-human animal models.

Advances in the design, creation and testing of more sophisticated vaccines have been stalled for several reasons. First, only a small number of vaccines can be tested in humans, because, understandably, there is little societal tolerance for harmful side effects in healthy people, especially children, exposed to experimental vaccines. With the exception of cancer vaccine trials, this greatly limits the innovation that can be allowed in the real world of human clinical trials. Second, it remains challenging to predict which epitopes are optimal for induction of immunodominant CD4 and CD8 T cell responses and neutralizing B cell (antibody) responses. Third, small animal testing, followed by primate trials, has been the mainstay of vaccine development; such approaches are limited by intrinsic differences between human and non-human species, and ethical and cost considerations that restrict the use of non-human primates. Consequently, there has been a slow translation of basic knowledge to the clinic, but equally important, a slow advance in the understanding of human immunity in vivo.

SUMMARY OF THE INVENTION

The in vivo immune model of the present invention can be used to address this inability to test many novel vaccines in human trials by instead using human cells transplanted into mice. The present invention also enables rapid vaccine assessments both in vitro and in vivo in models of aspects of the human immune system. The present invention also enables the generation of human monoclonal and polyclonal antibodies in mice.

The present invention comprises both in vitro and in vivo models of aspects of human immunity that are useful for assessing the interaction of substances with the immune system, and thus can be used to accelerate and improve the accuracy and predictability of, for example, vaccine, drug, biologic, immunotherapy, cosmetic, and chemical development. The present invention also comprises a means of developing fully human monoclonal and polyclonal antibodies in a mouse. The present invention shows that three- and four-way interactions of dendritic cells, B cells, T cells, and optionally follicular dendritic cells (FDCs) in a defined sequential order of events are important (i.e., that the timing of immunological events is important to stronger immune responses) both in vivo and in vitro.

DESCRIPTION OF THE INVENTION

Definitions

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order, unless otherwise indicated herein or otherwise clearly contradicted by context.

As used herein, the term "immune cells" refers to peripheral blood lymphocytes (PBLs), or peripheral blood mononuclear cells (PBMCs). The term includes T cells, B cells, monocytes and dendritic cell precursor.

As used herein, the term "immunocompetent" refers to the normal bodily capacity to develop an immune response following exposure to an antigen.

As used herein, the term "peripheral blood lymphocytes (PBLs)" refers to mature lymphocytes (small white immune cells) that are found circulating in the blood as opposed to organs, such as the lymph nodes, spleen, thymus, liver or bone marrow.

As used herein, the term "responder" refers to the response to a vaccine. As used herein, high, low, and moderate responders are those subjects with high, low, and moderate immunodominant CD4 and CD8 T cell responses and neutralizing B cell (antibody) responses.

As used herein, the term "vaccine" refers to an antigenic composition that is used to establish immunity to a disease, prophylactically or therapeutically, and includes a composition that induces immunodominant CD4 and/or CD8 T cell and/or neutralizing B cell (antibody) responses. The composition can further comprise other pharmaceutically acceptable ingredients. Many pharmaceutically acceptable ingredients are known in the art and contemplated for use in the methods disclosed herein.

The invention disclosed herein comprises a human immune model system comprising an irradiated mouse, wherein the irradiated mouse comprises a) radiation-resistant follicular dendritic cells (FDCs); b) a population of human PBLs; and, c) antigen/antibody immune complexes, wherein the mouse is immunocompetent before irradiation. In another aspect, a method is described herein for producing the human the immune model system, comprising a) culturing in vitro human T cells with antigen-pulsed dendritic cells (DC) for sufficient time to produce primed $CD4^+$ helper T cells in a T cell/DC culture to produce a T/DC population; b) combining antigen-pulsed human B cells with the in vitro T cell/DC population of part a) to produce a B/T/DC population; c) inserting the B/T/DC population of part b) into the lymph system of an irradiated mouse, wherein the mouse is immunocompetent before irradiation; whereby the irradiated mouse comprising the B/T/DC population is a human immune model system.

The invention is also directed to a method of producing human antibodies comprising collecting the antibodies produced by the human immune model system disclosed herein, wherein the antibodies are polyclonal antibodies. In one embodiment the method further comprises a) immortalizing B cells obtained from the human immune model system to produce hybridomas; b) cloning each hybridoma; and c) culturing each hybridoma to produce monoclonal antibodies; and, d) collecting the monoclonal antibodies.

The invention further includes a method of determining the effect of a candidate composition in a human immune model system comprising a disease, the method comprising: a) contacting an irradiated mouse comprising a human immune model system of claim 1 and a disease with the candidate composition; and, b) determining the effect of the candidate composition on the response of the human immune model system to the disease; wherein when the candidate composition alters the response of the human immune model system to the disease, the effect of the candidate composition is determined. In one embodiment, the candidate composition is selected from the group consisting of vaccines, adjuvants, immunotherapy candidates, cosmetics drugs, biologics, other chemicals and combinations of any of the foregoing. In another embodiment, the effect determined is therapeutic efficacy. In an embodiment, the effect determined is prophylactic efficacy. In one embodiment, the effect determined is toxicity. In yet a different embodiment, the effect determined is dose effect. In the method of the invention, the disease is infectious. In one embodiment, the infectious disease is one of avian flu, SARS, HIV, West Nile virus, influenza, lassa, malaria, yellow fever, hepatitis A, B and C, tuberculosis, smallpox, herpes, Ebola, dengue fever, chickenpox, measles, mumps and rubella. In a different embodiment, the disease is a tumor or a cancer.

The invention is also directed to a method of determining the effect of a candidate composition on a human immune model system, the method comprising: a) contacting an irradiated mouse comprising a human immune model system of claim 1 with the candidate composition; and, b) determining the effect of the candidate composition on the response of the human immune model system; wherein when the candidate composition alters the response of the human immune model system, the effect of the candidate composition is determined. In one embodiment, the candidate composition is selected from the group consisting of vaccines, adjuvants, immunotherapy candidates, cosmetics drugs, biologics, other chemicals and combinations of any of the foregoing. In a particular embodiment, the effect determined is toxicity. In another embodiment, the effect determined is dose effect.

The invention is also directed to a method of producing a human immune response comprising contacting an irradiated mouse of claim 1 with a composition comprising at least one antigen, wherein the irradiated mouse produces a human immune response to the at least one antigen in said composition. In one embodiment, the human immune response is a primary antibody response by B cells. In another embodiment, the antigen is selected from the group consisting of tumor cells, biopsy samples, PMBCs, and proteins. The method further comprises obtaining the antibodies produced to at least one antigen. In one embodiment, the antibodies are polyclonal. In another embodiment, the method further comprises isolating a population of B cells, immortalizing the B cells to form hybridomas, isolating each hybridoma, and obtaining monoclonal antibodies.

The invention also includes a method of enhancing B cell function comprising: a) prepulsing dendritic cells with antigen in the presence of T cells to obtain a T/DC/Ag cell population; b) prepulsing B cells with antigen followed by removal of the antigen to obtain a B cell population (B-Ag); c) combining the T/DC/Ag cell population of part a) with the B-Ag cell population of part b) after a predetermined amount of time to obtain a T/DC+B-Ag system; and, d) determining the number of antigen-antibody responses in the T/DC+B-Ag system; wherein the number of antigen-specific antibody responses in the T/DC+B-Ag system is greater than the number of antibody-antigen responses obtained from a T/B/DC/antigen co-culture system. In one embodiment, the predetermined amount of time is about 24 hours.

The invention also includes a method of enhancing B cell function comprising a) prepulsing dendritic cells with antigen in the presence of T cells to obtain a T/DC/Ag cell population; b) prepulsing B cells with antigen-prepulsed DCs, to obtain a B cell-dendritic cell population (B-DC); c) combining the T/DC/Ag cell population of part a) with the B-DC cell population of part b) after a predetermined amount of time to obtain a T/DC+B-DC system; and, d) determining the number of antigen-antibody responses in the T/DC+B-DC system; wherein the number of antigen-specific antibody responses in the T/DC+B-DC system is greater than the number of antigen-antibody responses obtained from a T/B/DC/antigen co-culture system.

The invention is also directed to a method of screening the efficacy of a candidate vaccine in a population comprising a plurality of individual subjects, the method comprising a) obtaining a sample of immune cells from each of a plurality of the subjects to obtain a subject-specific immune cell sample comprising subject-specific B cells and subject-specific T cells; b) priming each of the subject-specific T cell samples by exposure to the candidate vaccine to obtain a subject-specific primed T cell population; c) combining each subject-specific primed T cell population with each subject-specific B cell population to obtain a plurality of primed immune cell populations, wherein the T cell and B cell population is from the same subject; d) populating a plurality of irradiated mice with the plurality of primed immune cell populations of part c), wherein each irradiated mouse is populated with a single primed immune cell population to obtain a plurality of populated mice, wherein each mouse was immunocompetent prior to irradiation; e) characterizing the response of each immune cell population in the plurality of populated mice to obtain a plurality of subject-specific responses; and, f) determining the proportion of subjects in the population which are high, moderate or low responders to the candidate vaccine, whereby the efficacy of a candidate vaccine is screened. In one embodiment, the population comprises 50-100 subjects. In another embodiment, the subjects are human. In a different embodiment, different formulations of the same vaccine are screened. In a preferred embodiment, the method further comprises repeating the method with immune cells from high responders and a different vaccine or vaccine formulation. In another preferred embodiment, the method further comprises repeating the method with immune cells from moderate responders and a different vaccine or vaccine formulation. In yet a different preferred embodiment, the method further comprises repeating the method with immune cells from low responders and a different vaccine or vaccine formulation.

The present invention is directed to methods for constructing models of aspects of human immunity and, in particular, construction of a human immune system model for testing of vaccines, adjuvants, immunotherapy candidates, cosmetics, drugs, biologics and other chemicals. The present invention comprises both in vivo and in vitro models of aspects of human immunity that are useful for assessing the interaction of substances with the immune system, and thus can be used to accelerate and improve the accuracy and predictability of, for example, vaccine, drug, biologic, immunotherapy, cosmetic and chemical development.

There remains a long-standing need for in vivo or in vitro technologies that make it possible to rapidly assess vaccines. Furthermore, such technologies should enable the testing of experimental vaccines in model systems that are predictive of the human immune response in vivo. Diseases like avian flu, bioengineered threats, or new (newly appreciated) infectious diseases (e.g., SARS, HIV, West Nile virus, Ebola virus) emerge rapidly. The quicker the response of human immune system cells to a potential vaccine can be evaluated, the better.

Our studies demonstrated that murine FDCs can provide accessory cell activity for human $CD4^+$ T and B cells to interact and form germinal centers (GCs) and produce specific antibodies (Fakher et al. (2001) *Eur J Immunol* 31, 176-85). However, both human and murine responses in vivo are stronger than those we had achieved in vitro.

In an embodiment, the present invention comprises the use of human immune cells in mice that have been irradiated, so as to kill the vast majority of murine lymphocytes. Murine FDCs are largely radiation-resistant. Thus, the present invention comprises human lymphocytes added to an irradiated mouse; the combination of the surviving murine FDCs with the added human lymphocytes provides a model system that can be used for vaccine assessment.

In published work, antigen has been used to stimulate human responses in mice transplanted with human cells, but responses have been low-to-undetectable. Humanized SCID mouse models have been used, but the responses have been very low, they use a lot more human cells, they take a lot of time (a month or more), are expensive, and need special facilities for containment.

In an embodiment, the present invention provides a system that is cost-effective, rapid, and provides strong responses, because the antigen is directed to the FDCs in follicles that develop germinal centers (GCs) where immune responses normally take place. In contrast, SCID mice lack FDCs and they develop slowly upon exposure to B cells. By use of the mouse model, we have shown that ~20 million $CD4^+$ T cells and ~15 million B cells are apparently sufficient to provide the specific cells necessary for a human anti-OVA primary immune response.

In an embodiment of the present invention, cells from a person with ~200 ng of serum antibody were able to give ~500 ng in two weeks when immune complexes were used to load FDCs, while antigen alone failed to induce a detectable response (see FIG. 16). This difference in responsiveness is important. Another difference is that we inject both the immune complexes and human lymphocytes behind the animal's neck from where they flow into draining lymph nodes, rather than into the spleen via the blood.

We were able to prime human T cells in vitro and use them with immune complexes in a murine system to generate a strong, specific primary antibody response including class switching to IgG in the lymph node (FIG. 17). Thus, this embodiment of the present invention would be suitable for testing responses of human leukocytes to vaccines outside the human body. As the model of this embodiment provides an in vivo environment, it is also possible to study dose versus toxicity for vaccines and adjuvants.

Furthermore, the in vivo aspect of this embodiment of the invention could be used for examining dose-dependent toxic effects of immunosuppressive agents, while establishing their ability to inhibit human antibody responses. Similarly, toxic drugs including chemotherapeutics (e.g., for cancer), certain antibiotics, and other chemicals could be studied over a dose range for their impact on humoral immunity in a model human system without risk to human health.

It should also be appreciated that in another embodiment of the present invention, about 50 to about 100 mice or more can rapidly be set up with leukocytes from about 50 to about 100 or more different individuals and rare problems can be detected using this model, whereas variations in humanized mice models that are currently available are very limited. Specifically, FDCs do not develop in SCID mice and humanized SCID mice would not be expected to work by means of immune complexes being trapped on FDCs, as we demonstrate in this model.

Furthermore, in another embodiment this murine system could be used to examine the radiation effects on a human immune system in an in vivo non-human manner. In another embodiment, human biopsies (e.g., tumors) could be taken from patients, along with their PBMCs; it would then be possible to directly examine therapeutic effects of various drugs and vaccines against the disease in the model.

Additionally, this model could also be adapted to make high-affinity human monoclonal antibodies for therapeutic approaches, and more generally, various human proteins (e.g., type 1 and type 2 interferons, cytokines, such as IL-2, IL-4, IL12). For monoclonal antibodies, it is of special interest that B cells in GCs are known to somatically hypermutate and the high affinity cells are selected for survival. Use of human cells in a murine GC could lead to production of high affinity monoclonal antibodies that are not currently available in the human system. A major clinical benefit of such high affinity antibodies is that it can provide therapeutic benefit at low concentrations. Typically, low affinity antibodies must be present in high concentrations and may not work at all.

Our recent work indicates that FDCs promote somatic hypermutation and select the high affinity B cells for survival, leading to affinity maturation. Thus, if human B cells hypermutate in the murine germinal centers, this model could provide a unique and cost-effective way to make these very important proteins with high affinity that could exert beneficial therapeutic effects at low concentrations.

Use of the in vivo model of the present invention allows us to examine how many naïve B and T cells are necessary to get a primary response. In addition, timing of the specified immunocyte interactions appears to influence immunological behavior. For example, our results indicate that stronger responses are obtained when T cells are cultured with antigen-pulsed DCs for several days before, allowing the DCs to optimally present the antigen and prime the $CD4^+$ helper T cells. At the end of this DC/T cell culture (of the order of ~1 to ~7 days), B cells are be added to the in vitro antigen-primed T cells. Under physiological conditions within lymph nodes, the generation of antigen-specific T cells by DCs in the paracortex usually occurs before the induction of specific B cell responses in the cortex. The present invention mimics this sequence of events.

The in vivo model of the present invention is suitable for testing the responses of human cells to vaccines, adjuvants, chemicals, and other drugs outside the human body. Furthermore, because the analysis takes place in vivo, it could be used to examine dose and toxicity effects at the same time. Additionally, disease models can also be included in the mouse to test the efficacy of either therapeutic or prophylactic therapies with regard to infectious disease.

The in vivo models of the present invention that deal with timing of the leukocyte cell-cell interactions may lead to improved immune responses to activate and expand human antigen-specific T cells in vitro. Furthermore, helper T cells can be used to induce a more robust recall or naïve human antigen-specific antibody response in vitro. In vitro, two- and three-way interactions of the key cells (dendritic cells, B cells, T cells) in a defined sequential order are important (i.e., the timing of immunological events leads to stronger in vitro immune responses).

The murine system of the present invention can also be used as a source of valuable human proteins, including monoclonal antibodies. As an example, the system could also be used to immunize naïve cells from healthy donors with pathogenic threat agents. A major advantage of such a mouse model or an in vitro system is that the model system can be exposed to dangerous pathogens and produce human antibodies without risk to a human. It should also be possible to achieve to high affinity antibodies as a consequence of either in vivo or in vitro avidity maturation in the germinal center.

Germinal centers (GCs) are rich in certain leukocytes (e.g., B cells, $CD4^+$ T cells, FDCs), whereas other cell types are rich in other microenvironments (lymph node sinuses, deep cortical units, medullary cords: FIG. 1). Such compartmentalization, which is readily apparent in vivo is likely important for immune system function. Follicular dendritic cells (FDCs) are located in the follicles of secondary lymphoid tissue. They possess dendritic morphology, with numerous processes wrapped "spaghetti-like" and "beads" (iccosomes) seen on scanning electron micrographs (e.g., FIG. 2). FDCs bind and retain immune complexes (ICs). GC cells include FDCs, B cells and $CD4^+$ helper T cells. However, NK cell, $CD8^+$ T cells, PMNs, or monocytes, all of which are common in the blood, are rare or absent (FIG. 1).

When antibodies are formed in a primary immune response or upon secondary challenge, immune complexes (ICs) are formed. Immune complexes per se are poorly immunogenic but FDC accessory activity involves presenting the weakly immunogenic ICs in a highly immunogenic form to B cells and providing antigens for B cells to process and present to T cells (schematically illustrated in FIG. 3).

FDC accessory cell activity is apparently not MHC- or even species-restricted. In our experiments, murine FDCs can promote a human immune (IgG) response against tetanus toxoid (TT) after ~14 days (FIG. 4).

Most leukocytes appear to have resting and activated phenotypes; this seems to be true of FDCs too. Consequently, it may be important to activate the FDCs before setting up germinal center reactions.

In primary follicles, FDC-reticula can be found by labeling with anti-CR1/2, but FcγRIIB, ICAM-1, and VCAM-1 levels are very low and difficult to detect. FDCs in secondary follicles (with GCs) bear high levels of FcγRIIB, ICAM-1, and VCAM-1 and these molecules are involved in converting poorly immunogenic ICs into a highly immunogenic form for B cells and in facilitating FDC-B cell interactions required for optimal FDC accessory activity.

These relationships prompt questions about how FDCs are activated and what molecules participate in the activation process. Activated B cells are known to provide lymphotoxin and TNF, suggesting that B cell activation might lead to FDC activation and that could explain why FDCs associated with resting B cells exhibit a resting phenotype while those in active GCs express an active phenotype. However, in recall responses FDC activation is evident before B cell activation is apparent suggesting that the IC itself might play a role in activating FDCs. The data presented here are consistent with this (FIG. 5). The data suggest that it would be helpful to get FDCs activated (FcgRIIB upregulated) before placing the FDCs in culture with ICs, B cells, and helper T cells. A way of activating FDCs is by encountering ICs, suggesting we should add ICs and active FDCs at the beginning of the GC reaction (FIG. 6). In an embodiment of the present invention, ICs are added to the FDCs to activate them (upregulation of FcRIIB and adhesion molecules) before addition of lymphocytes.

EXAMPLES

Example 1

Antibody Response to an Experimental Vaccine

The mouse provides an in vivo model system that enables comparisons with other model systems in vitro.

Preparation of the mouse model of an embodiment of the present invention comprises:
  irradiating mice at 1,000 rad to destroy the murine T and B cells and clear out the lymph nodes. We reason it may be of importance to get rid of as many murine T and B cells as possible, so that human cells flowing through the lymphatics from the site of injection can enter the mouse follicles where a germinal center (GC) could be established.

we then injected ~16×10⁶ human red blood cells (RBCs) and PMNs intraperitoneally (i.p.) one day before the lymphocytes, to bind murine antibodies that would otherwise react with human CD4⁺ T cells and B cells and potentially clear them.

tetanus anti-tetanus immune complexes were then injected into four sites (the hind foot pads and front legs) using ~25 ng of tetanus toxoid (TT) plus ~150 ng of goat anti-TT per site, to form ICs that we expected to lodge on the follicular dendritic cells (FDCs) (goat anti-TT was used to avoid introducing any human anti-TT into the mice that could contribute to background). We believe that these ICs were trapped and retained by FDCs in the follicles.

we then infused ~8×10⁶ human PBL into each of the hind foot pads and front legs. These cells were obtained from people with a very low anti-TT titer (~300 to ~3,000 ng/ml). This is not a primary response and we reason that memory T cells will be present, though few memory B cells (nevertheless, we did not use naïve B cells in these experiments).

we bled the mice after ~7 days and the human IgG anti-TT response was in the ~100 to ~200 ng/mL range and the day 14 response was in the ~400 to ~480 ng/mL range.

Figure 1:
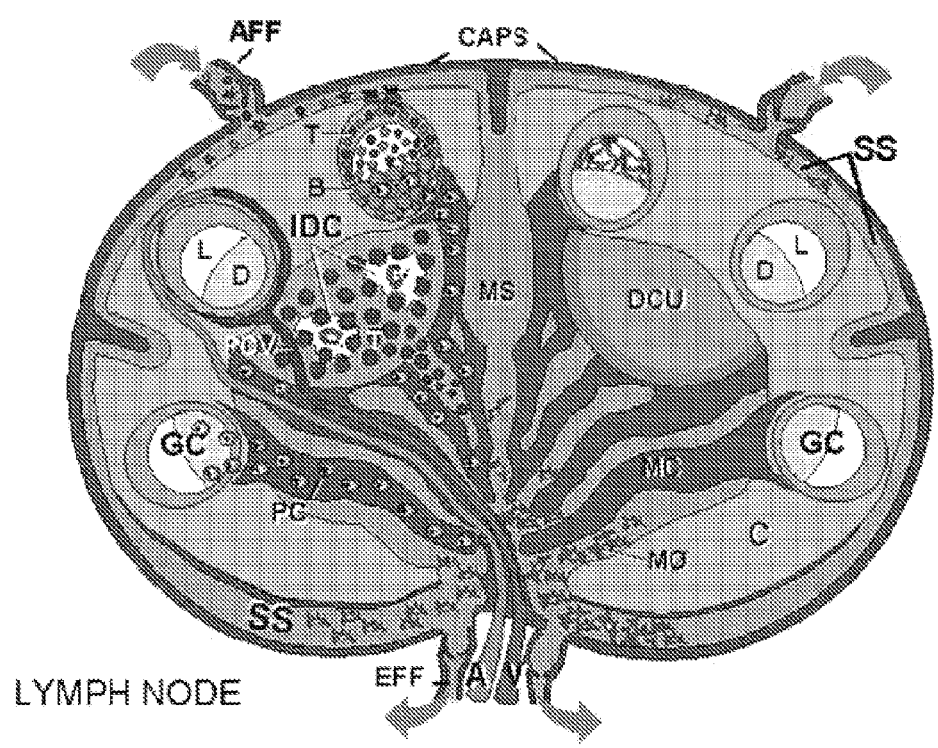
FIG. 1. Lymph node organization.
Figure 2:
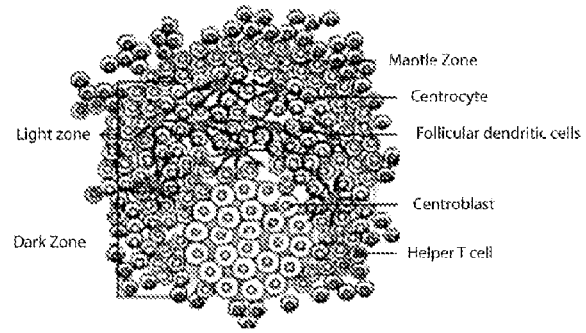
FIG. 2. Follicular dendritic cells (FDCs).
Figure 2:
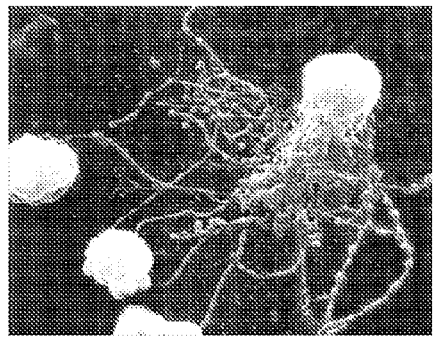
Figure 3:
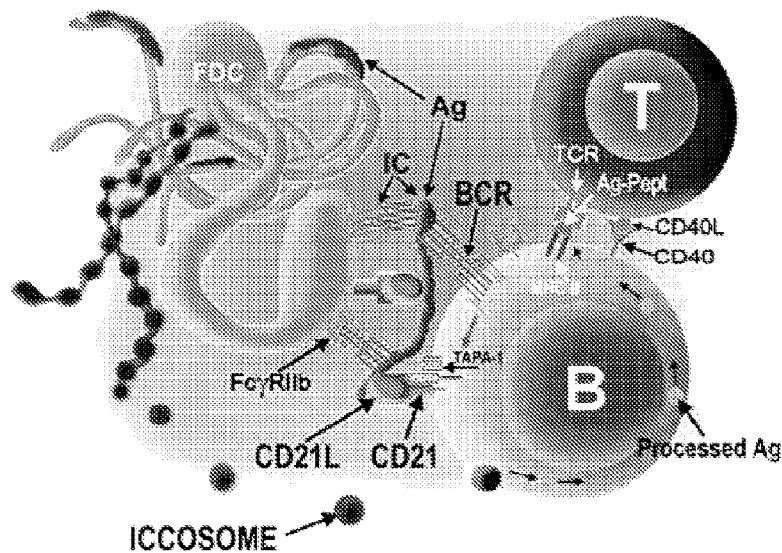
FIG. 3. Antibody response when FDCs are added to lymphocytes.
Figure 3:
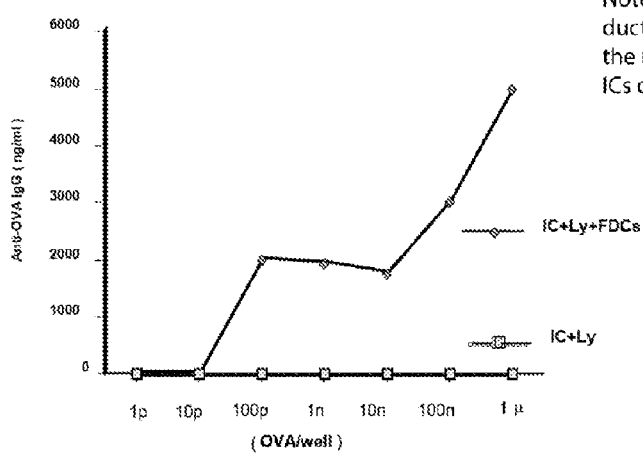
Figure 4:
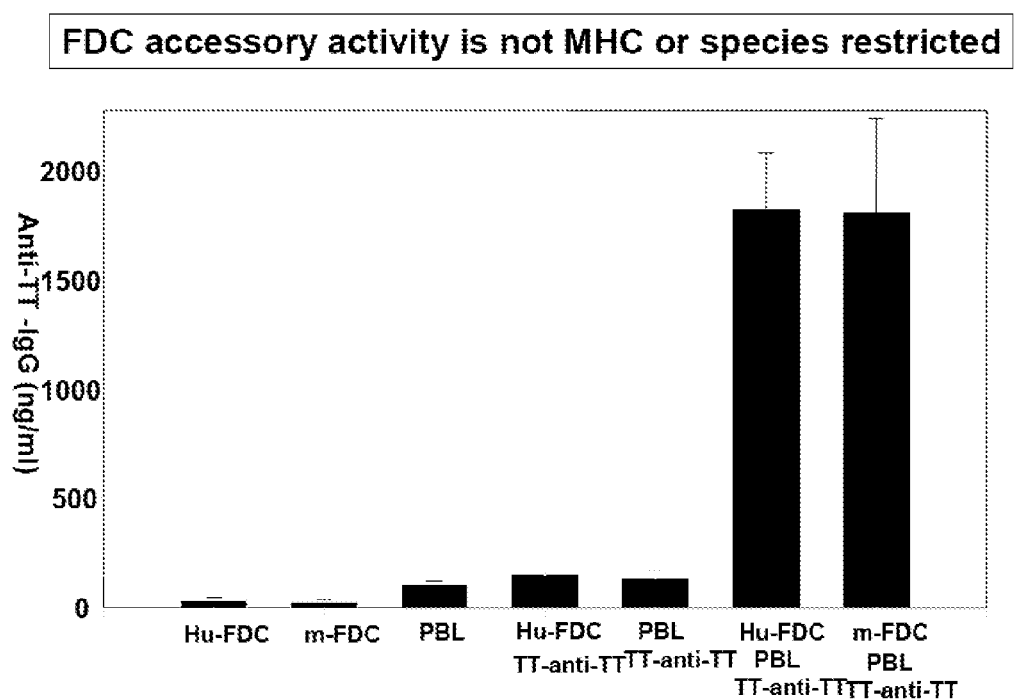
FIG. 4. FDC accessory cell function is apparently not MHC- or even species-restricted.
Figure 5:
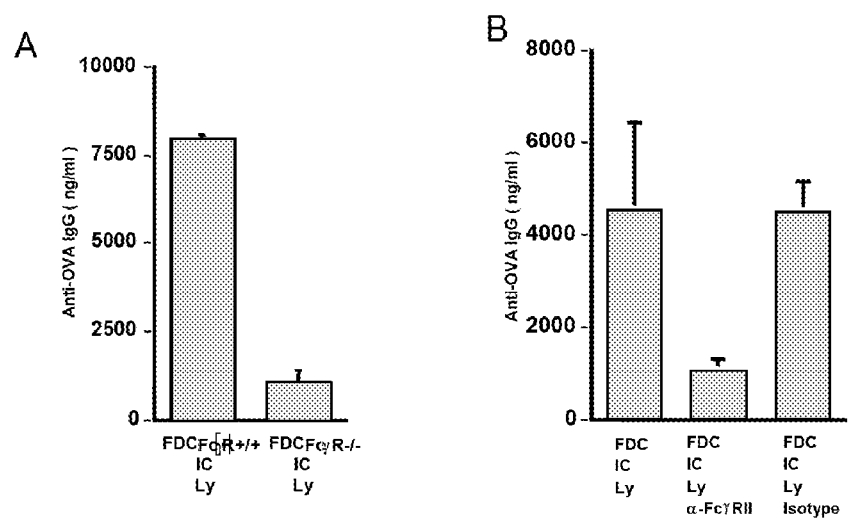
FIG. 5. In recall responses, FDC activation is evident before B cell activation is apparent, suggesting that the IC itself might play a role in activating FDCs.
Figure 6:
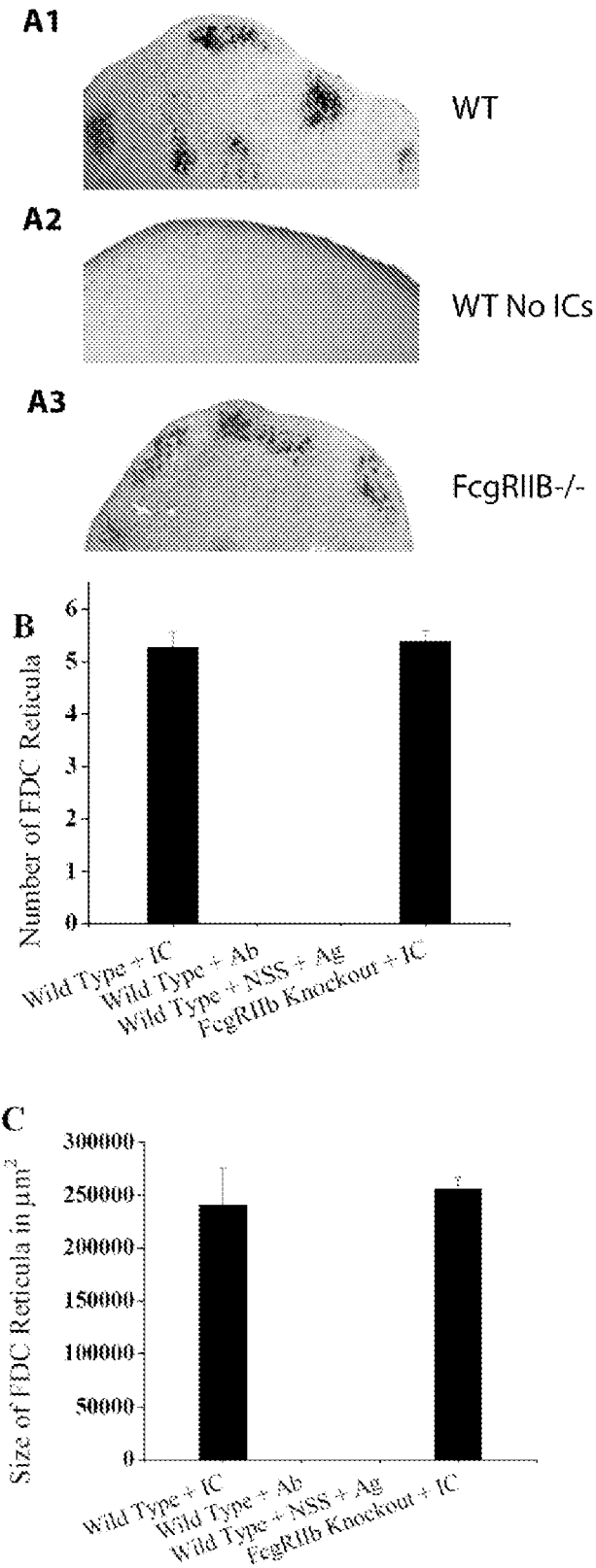
FIG. 6. Analysis of light micrographs illustrating trapping of IgG-OVA immune complexes (ICs) in FDC-reticula in draining axillary lymph nodes of mice.
Figure 7:
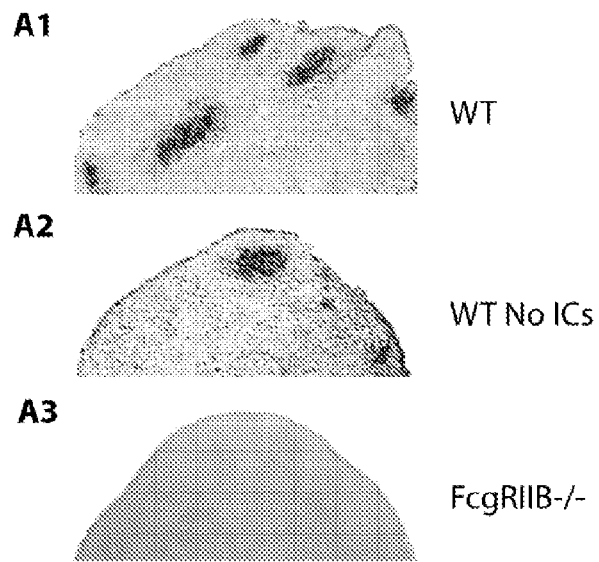
FIG. 7. Analysis of light micrographs of draining axillary lymph nodes illustrating immunohistochemical labeling of FDC-reticula with anti-FcγRIIB.
Figure 7:
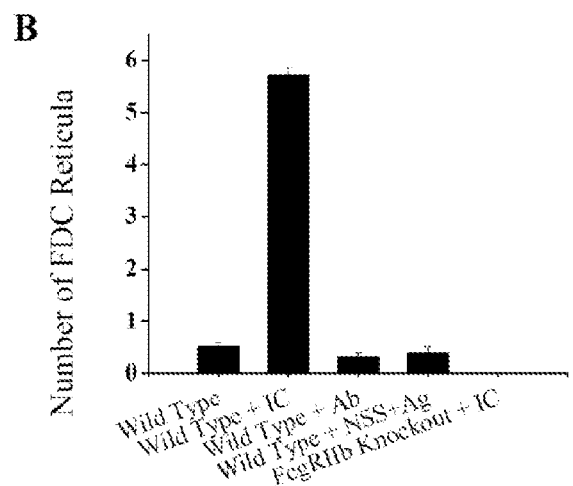
Figure 7:
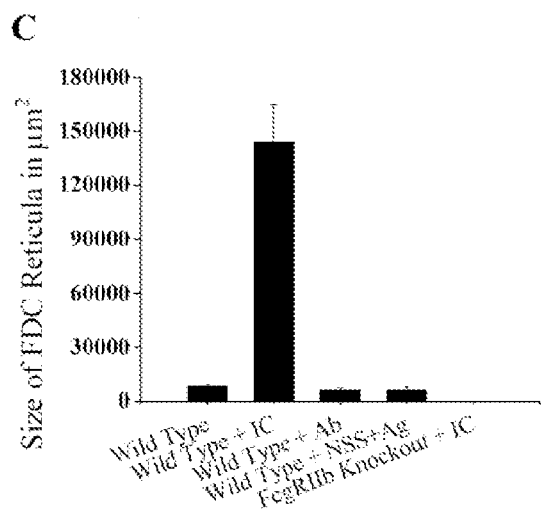
Figure 8:
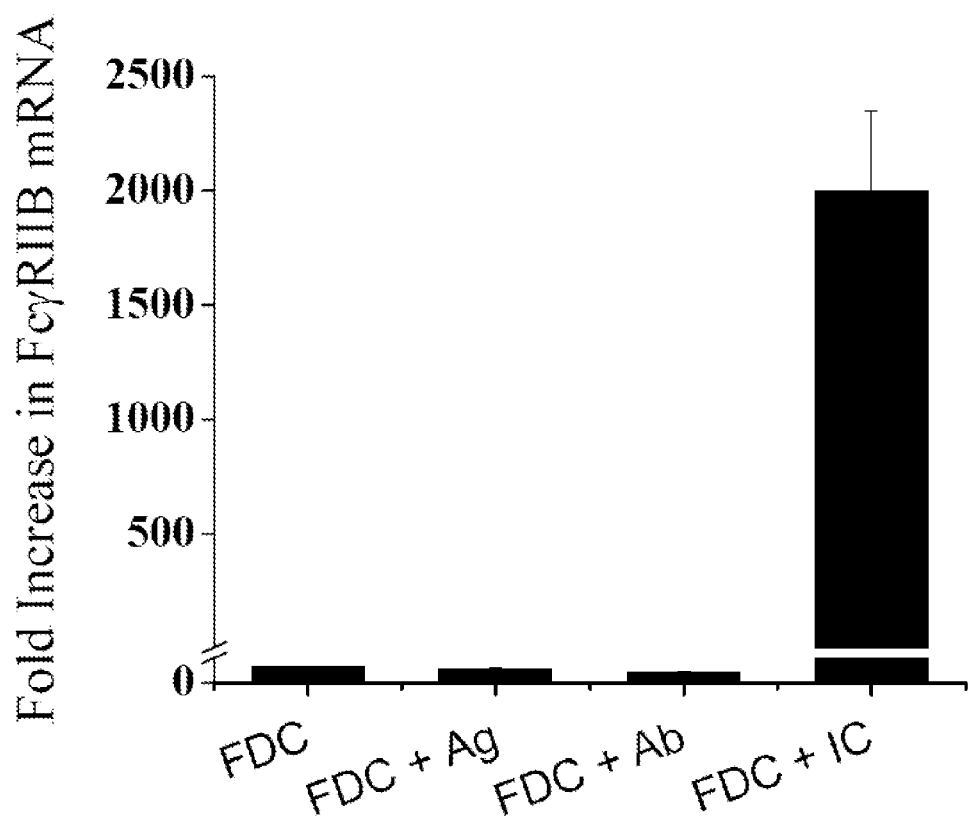
FIG. 8. Immune complex-mediated FcγRIIB-mRNA induction in FDCs.
Figure 9:
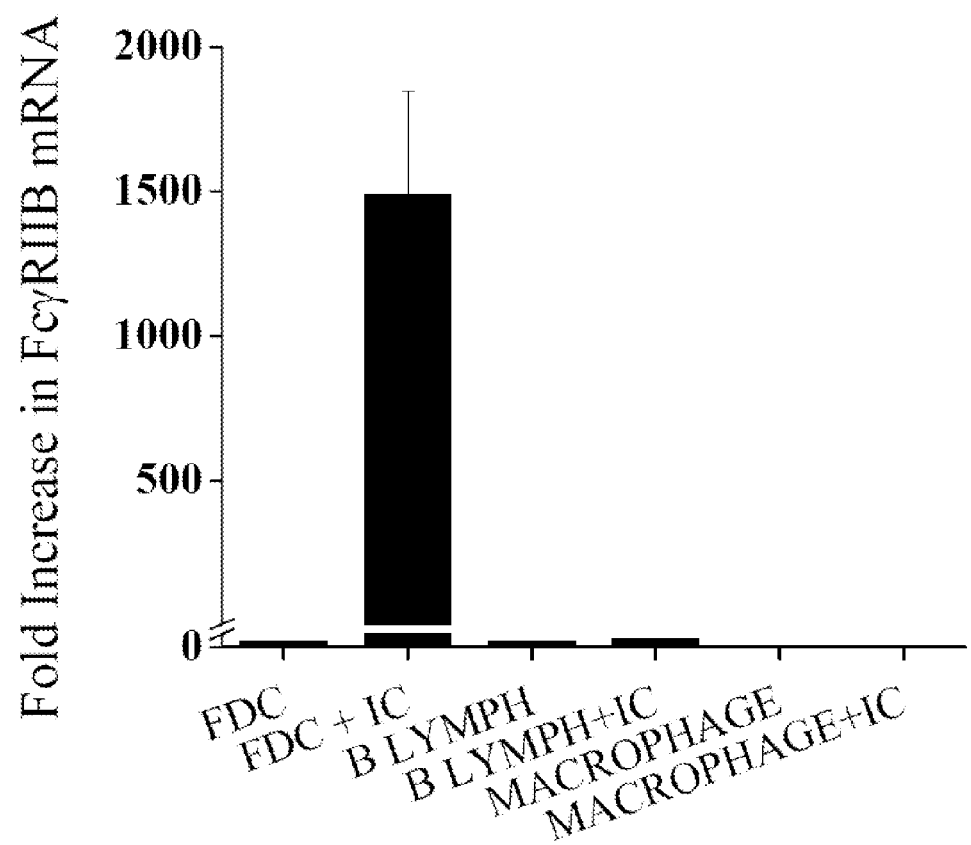
FIG. 9. Immune complex-mediated FcγRIIB-mRNA induction was not observed in B cells or macrophages.
Figure 10:
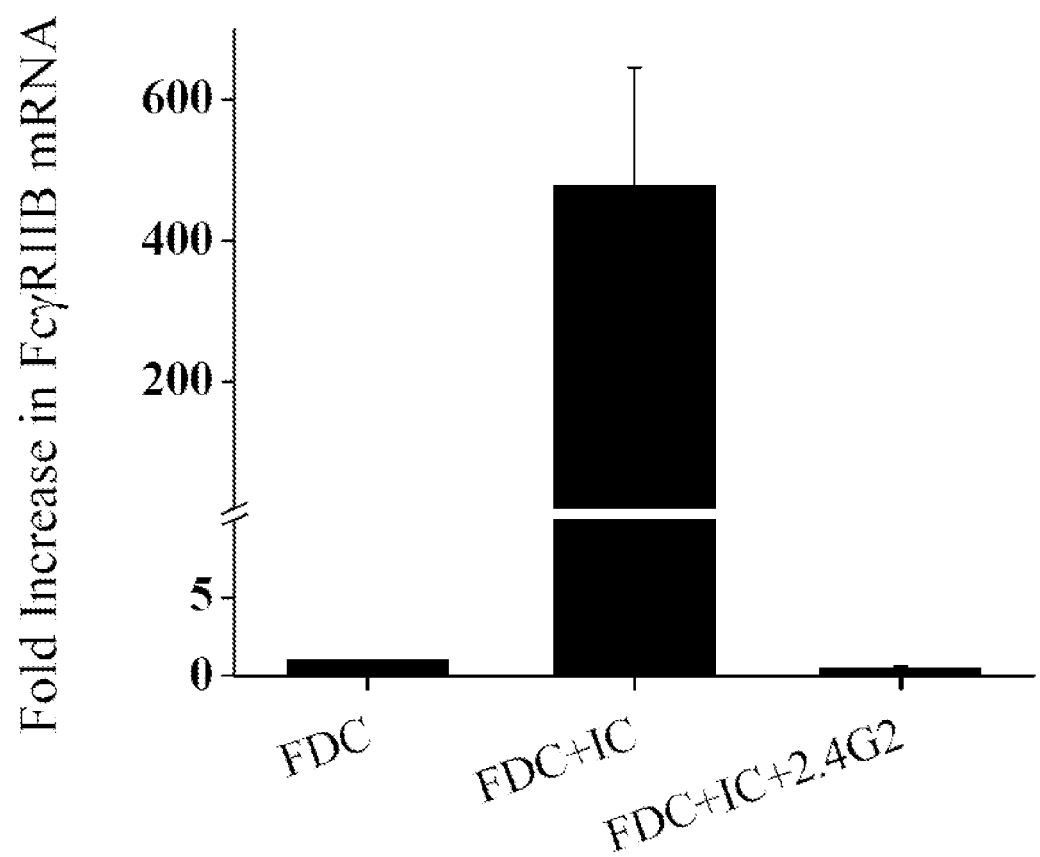
FIG. 10. Induction of FcγRIIB mRNA production in FDCs by ICs was blocked by anti-FcR (2.4 G2).
Figure 11:
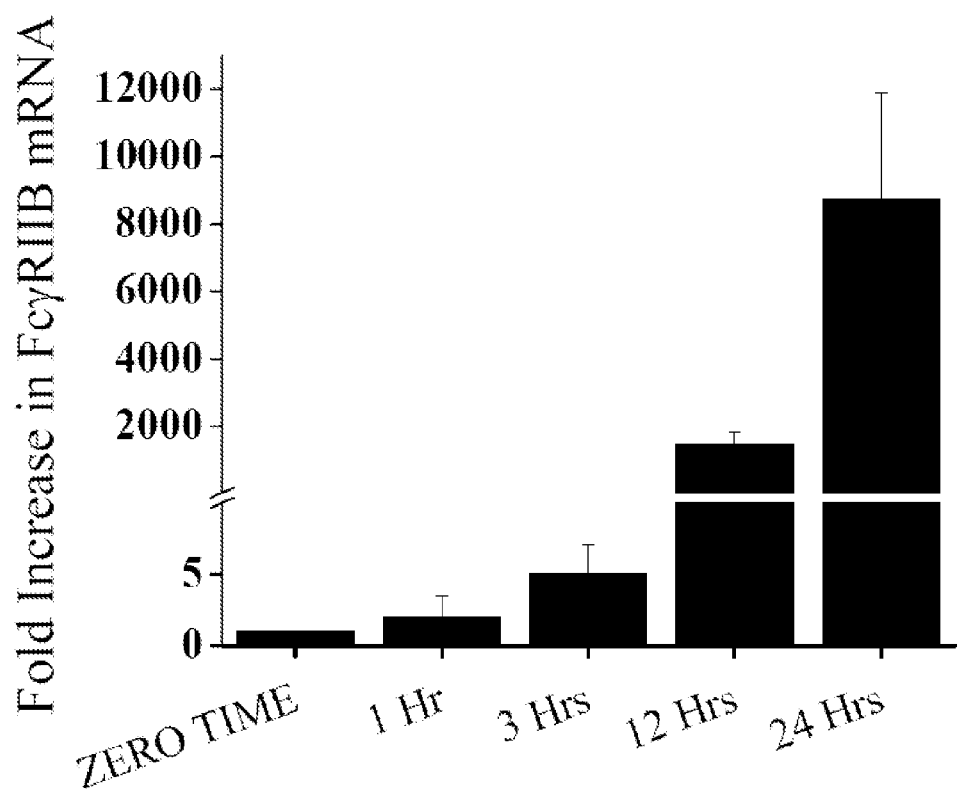
FIG. 11. Kinetics of IC-induced FcγRIIB mRNA production in FDCs.
Figure 12:
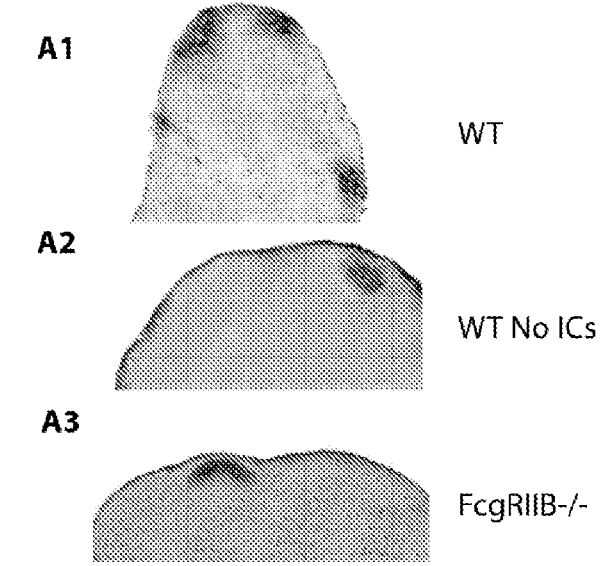
FIG. 12. Analysis of light micrographs of draining axillary lymph nodes, illustrating immunohistochemical labeling of FDC-reticula with anti-VCAM-1.
Figure 12:
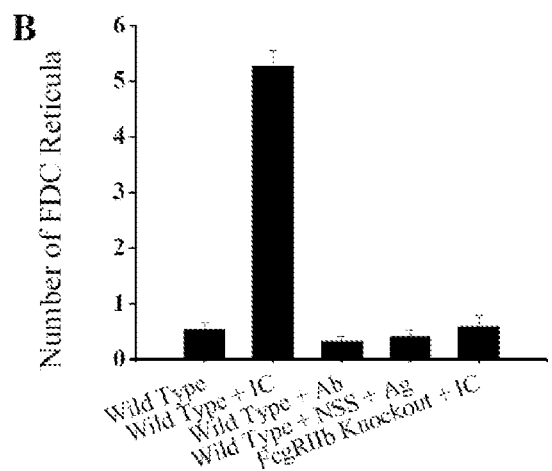
Figure 12:
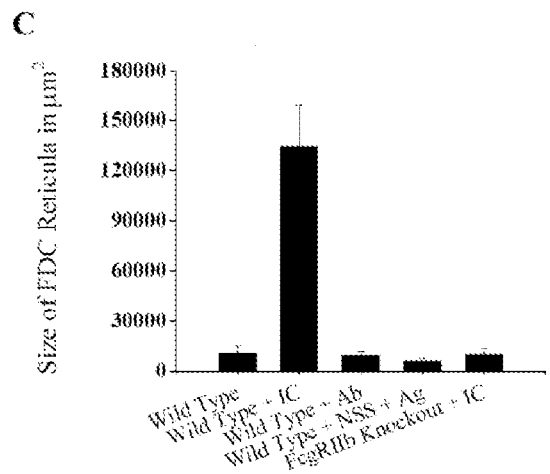
Figure 13:
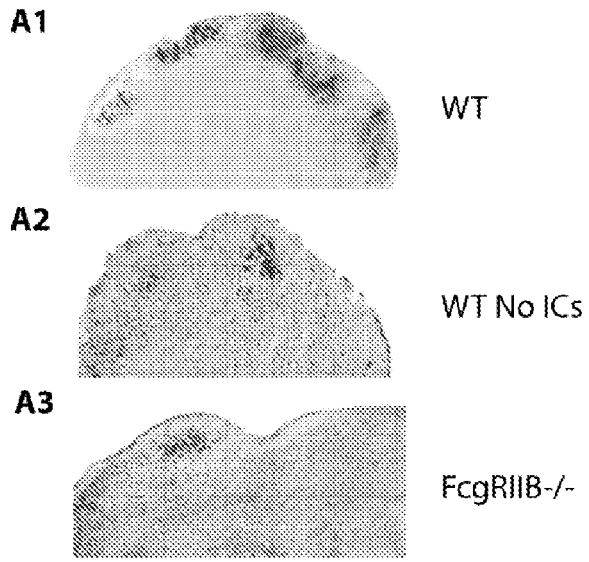
FIG. 13. Analysis of light micrographs of draining axillary lymph nodes, illustrating immunohistochemical labeling of FDC-reticula with anti-ICAM-1.
Figure 13:
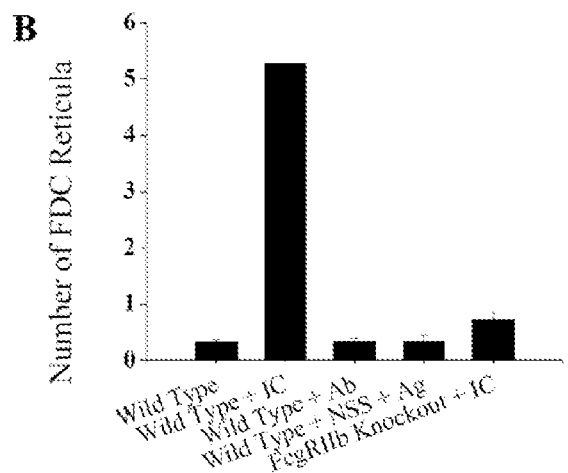
Figure 13:
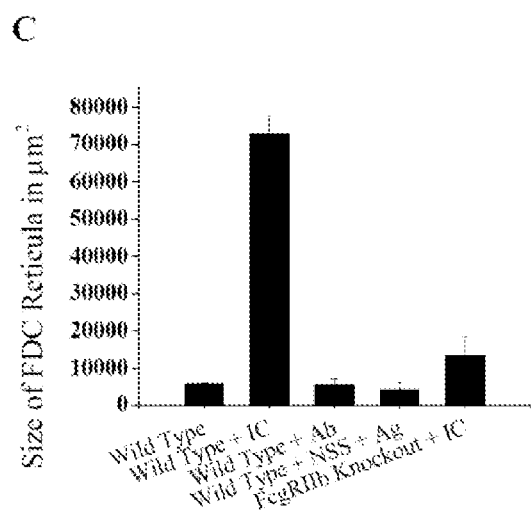
Figure 14:
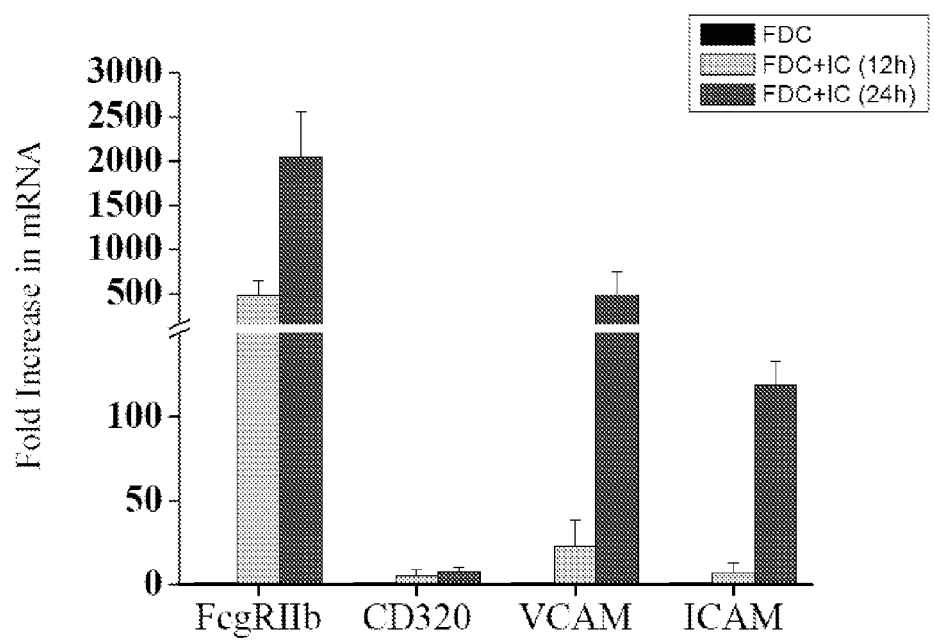
FIG. 14. Effect of IC-stimulation on mRNA related to FDC phenotype.

The ICs lodge on FDCs in the follicles, as illustrated (FIG. 14)

Example 2

The Model Immune System of the Present Invention can be Used in Vaccine Assessment CD4⁺ T cells and B cells can readily be obtained from many human subjects. T cells can be primed by exposure to various forms of an experimental vaccine or vaccine formulation and then injected with the B cells into lethally irradiated mice with the vaccine loaded on FDCs in vivo.

This model immune system can be used to answer many questions including, for example, how many people could potentially respond to a given vaccine or vaccine formulation, what proportions of the population are high, moderate, and low responders, and whether the same people respond to different forms of the same vaccine or do some people respond to one formulation and others respond to other formulations.

Example 3

Because many animals did not survive for 14 days when irradiated at 1,000 rad, the radiation dose was reduced to 600 rad. This improved survival. The experiment conducted was as follows:

mice were irradiated at 600 rad to destroy the murine T and B cells and clear out the lymph nodes.

we then injected ~16×10⁶ human RBCs and PMNs i.p. one day before the lymphocytes, to bind murine antibodies that would otherwise react with human CD4⁺ T cells and B cells and potentially clear them.

tetanus toxoid and goat anti-tetanus immune complexes were injected into four sites (the hind foot pads and front legs) or i.p. to load the spleen (goat anti-TT was used to avoid introducing any human anti-TT into the mouse, which could contribute to background).

in this example, we then injected total PBMC rather than the purified CD4⁺ cells and B cells. We did this to examine whether irrelevant cells would pass by the follicles and not cause a problem in vivo (whereas they appear to be a problem in in vitro cultures where they are always in the immediate vicinity).

we then injected PBMCs i.p. to stimulate the response in the spleen and we injected into the four legs to force cells to go through the lymphatics and draining lymph nodes. Our hypothesis was that the cells would get into follicles better in the draining lymph nodes and the response in the lymph nodes would be better than in the spleen.

Figure 15:
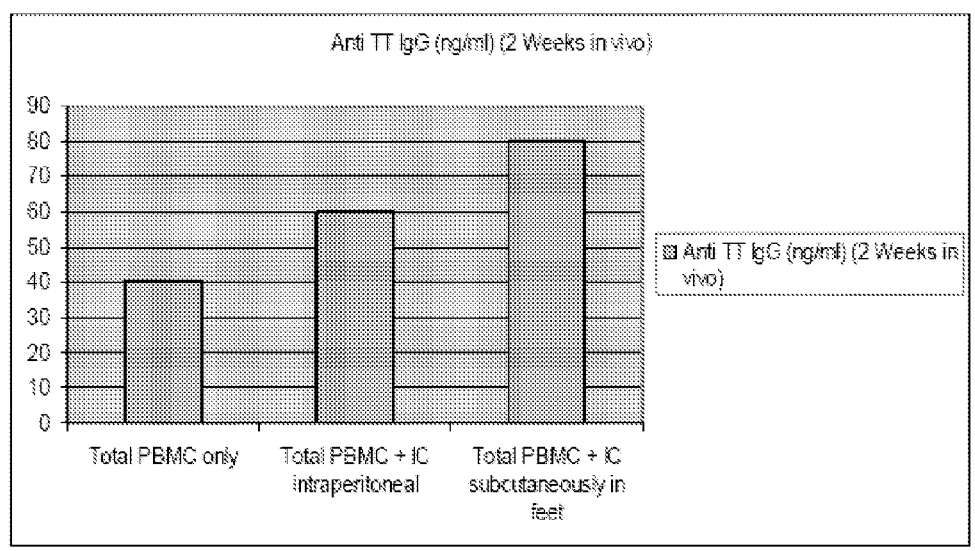
FIG. 15. Anti-TT IgG (ng/mL) after 2 weeks in vivo.

As FIG. 15 illustrates, there is considerable background without any ICs in the system. A stronger response was obtained from a donor with a lower serum anti-TT level (~200 ng/mL) when transferred cells were restricted to CD4⁺ T cells and total B lymphocytes. This suggests that the CD8⁺ cells, CD14⁺ cells, and CD56⁺ (NK cells) may be inhibitory or interfering in some way in vivo, as they do in vitro.

It appears that feeding cells into subcutaneous sites where they will go through draining lymph nodes leads to stronger responses than does injecting cells i.p. to stimulate responses in the spleen.

Example 4

Human Primary Antibody Response Including Class Switching and Production of Specific IgG (T Cell Priming In Vitro with B Cell Priming and Differentiation In Vivo)

Figure 16:
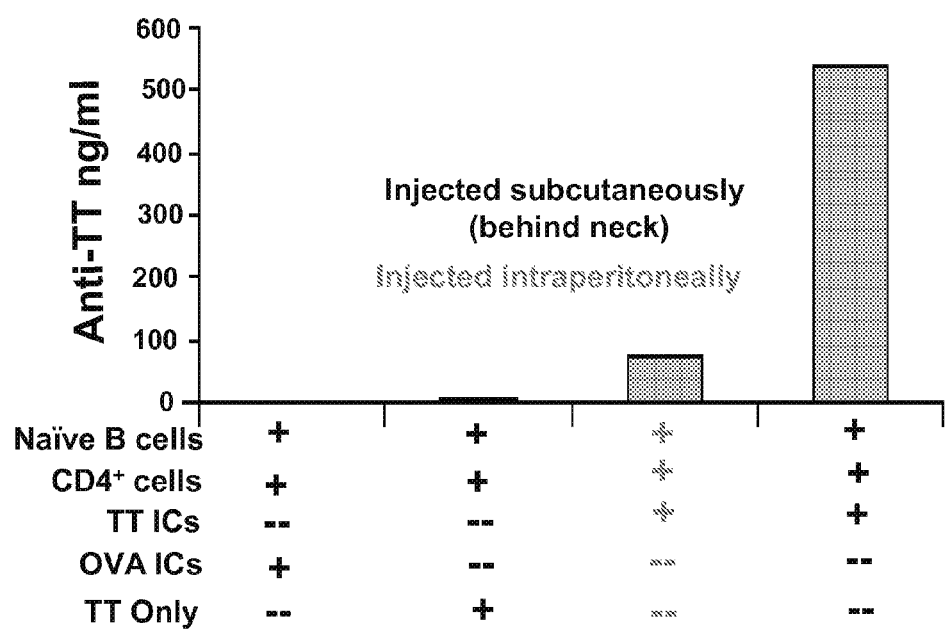
FIG. 16. Induction of anti-TT IgG by naïve B cells (this donor had ~200 ng/mL IgG anti-TT, so memory T cells were likely present in the donor's blood).

Loading ICs on lymph node FDCs provided a germinal center (GC) environment for getting naïve B cells to differentiate, class switch, and produce TT-specific IgG. These experiments were conducted by removing all B cells bearing IgG receptors, leaving IgM-expressing naïve B cells that would need to class switch to make IgG (see FIG. 16). These results illustrate that:

injecting the cells and ICs i.p. to load splenic FDCs gave a response but a weaker one than by injecting subcutaneously to load the lymph nodes (column 3 versus 4), antigen alone gave no detectible response; antigen will bind specific B cells, but without signals from IC-bearing FDCs in the GCs, the response is too low to detect (column 2), and specificity is evident because OVA-anti-OVA ICs do nothing to stimulate an anti-TT response (though not shown, OVA-anti-OVA does not induce any anti-OVA either in the absence of any OVA-specific T cell help).

Example 5

Priming T Cells and Inducing a Primary Human IgG Response

In this experiment:

~10×10⁶ monocytes were cultured in ~25 mL media supplemented with IL-4 (~1000 U/mL) and GM-CSF (~800 U/ml) to make immature DCs.

~3 days later another ~25 mL media supplemented with IL-4 (~1000 U/mL) and GM-CSF (~800 U/mL) were added and left for ~2 days to enhance DC differentiation (this appears to reduce monocyte marker CD14 and in our experience gives better DCs).

on day 5, ~50 µg LPS was added to the 50 mL medium (≈1 µg/mL)+~50 µg OVA (or CGG) were added to the ~50 mL medium (≈1 µg/mL), to provide antigen for processing and LPS for DC maturation.

after ~8 hours, ~20×10⁶ CD4⁺ cells were added and left for ~5 days to give the DCs time to present OVA and prime the CD4+ T cells. At the end of the ~5 days, the T cells and remaining DCs were spun down (T cell-DC clusters were still apparent).

~15×10$^6$ naïve B lymphocytes were isolated and added to the in vitro OVA-primed CD4s (this donor had no detectable serum anti-OVA when tested by ELISA).

OVA (~5 µg)+murine anti-OVA (~30 µg) were complexed (to form OVA ICs) and added to the cells and the mixture was brought up to ~1 mL.

The ~1 mL of cells and ICs were injected behind the neck of BALB/c mice that had been given LPS 3 days earlier (to activate FDCs) and irradiated with ~600 rad 24 hours before cell transfer (we believe that the ICs will load on the activated FDCs in draining lymph nodes and the T cells and B cells will home to the empty follicles under the influence of FDC chemokines).

Figure 17:
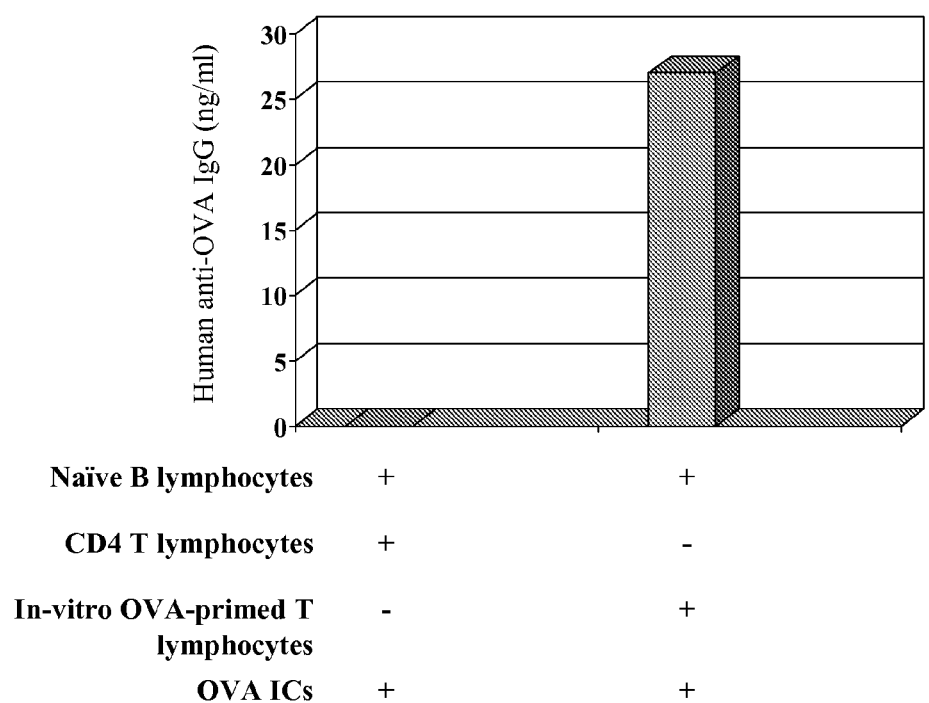
FIG. 17. Human primary antibody response, including class switching and production of OVA-specific IgG (note that in vitro-primed helper T cells worked, whereas naïve CD4 T cells did not).

~14 days later, serum was collected and human anti-OVA was quantified using an ELISA against a standard of human IgG (FIG. 17).

Thus, it appears that ~20×10$^6$ CD4+ T cells and 15×10$^6$ B cells are sufficient to provide the specific cells necessary for a human anti-OVA primary response. Additionally, priming of the T cells for longer periods (e.g., ~5 days or longer) helps to get functional helper T cells.

Example 6

Activation and Expansion of Human Antigen-Specific T Cells In Vitro and Their Use to Induce a Recall Human Antigen-Specific Antibody Response In Vitro To prime the T cells in vitro, an experiment was set up with monocyte-derived DCs:

~15×10$^6$ monocytes were cultured in 5 ml X-Vivo media supplemented with IL-4 (~25 ng/mL) and GM-CSF (~100 ng/mL) to make immature DCs in 3 wells of a 6-well plate.

Six days later, ~25 ng/mL of TNFα+1 µg/mL TT antigen or 10 µg/mL *Candida* antigen (Ca) were added to the medium, to provide antigen for processing and TNFα for DC maturation.

On day 7, DCs were isolated, spun down and washed with media. Then, ~2.5×10$^5$ T cells/well were cultured for 3 days with TT-pulsed DCs (~1:60) or Ca-pulsed DCs to present TT-antigen or Ca-antigen and to prime the T cells.

On day 10, ~2.5×10$^5$ B cells/well were added to the in vitro TT- or Ca-primed T cells+DCs culture. Additional TT-antigen (~100 ng/mL) or Ca-antigen (1 µg/mL) was also added to the culture to stimulate antigen-specific B cells.

Seven days after addition of the B cells, cells were isolated to analyze TT or Ca-specific proliferative response using flow cytometry and TT- or Ca-specific antibody responses using an ELISPOT assay.

Figure 18:
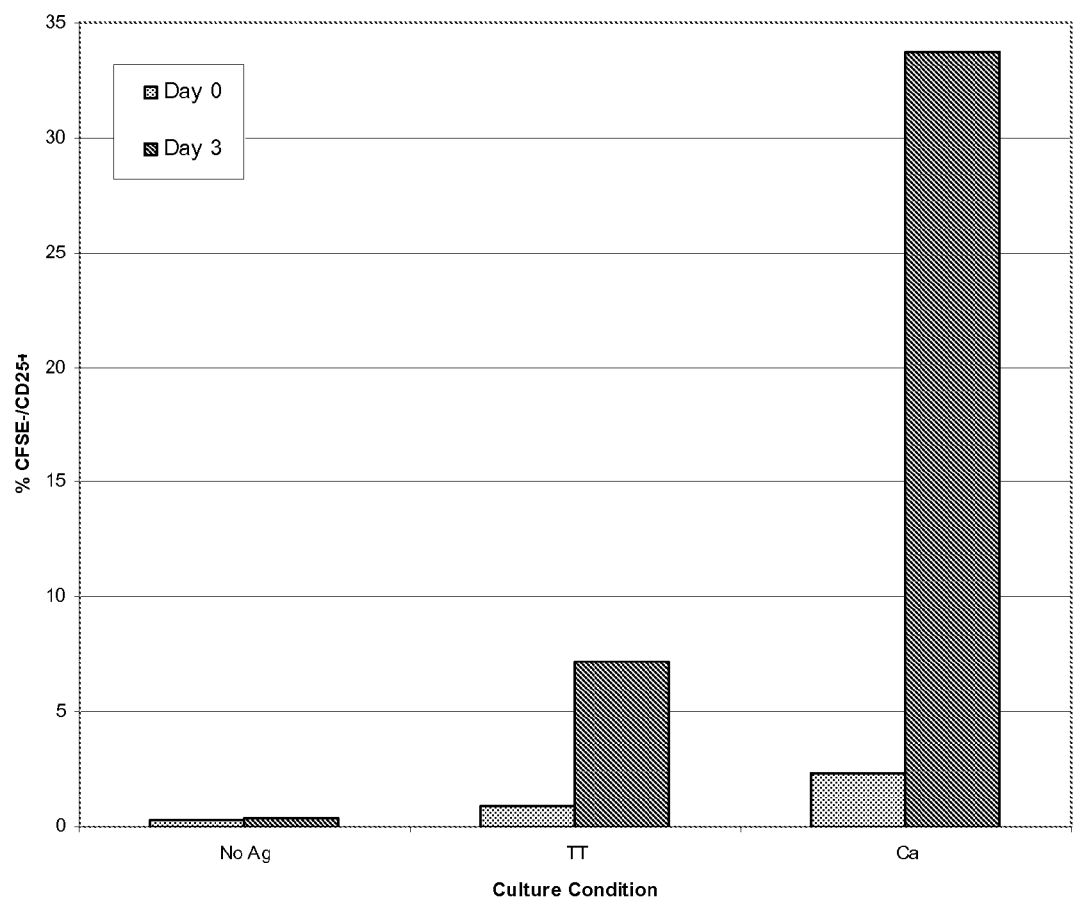
FIG. 18. T-cell proliferation: comparison between day 0 and day 3 for antigen-pulsed DC/T cell interactions.
Figure 19:
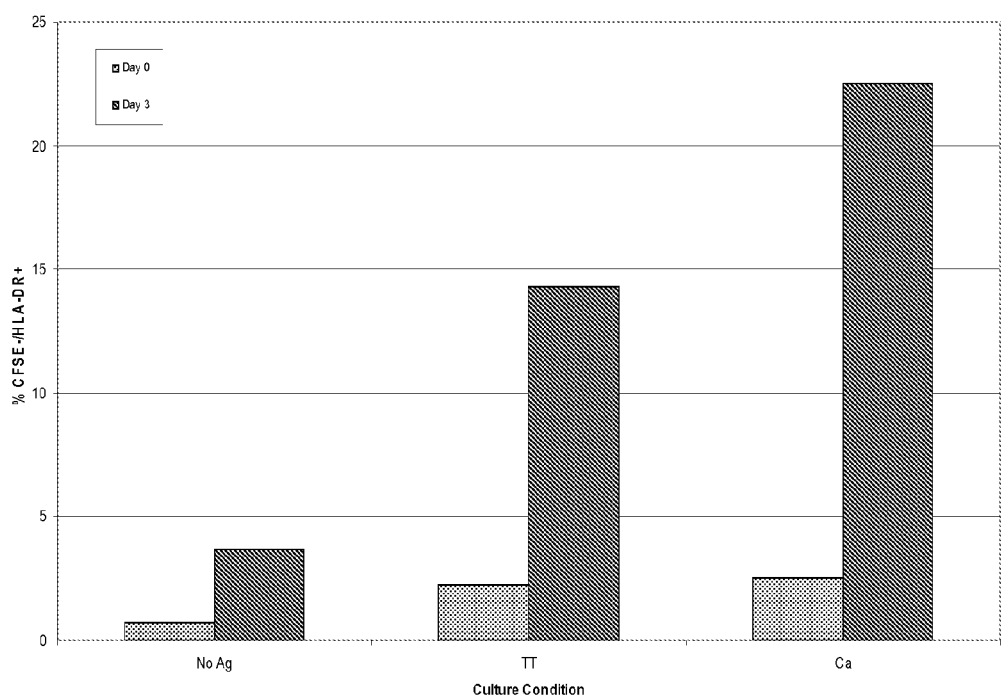
FIG. 19. B-cell proliferation: comparison between day 0 and day 3 for antigen-pulsed DC/T cell interactions.
Figure 20:
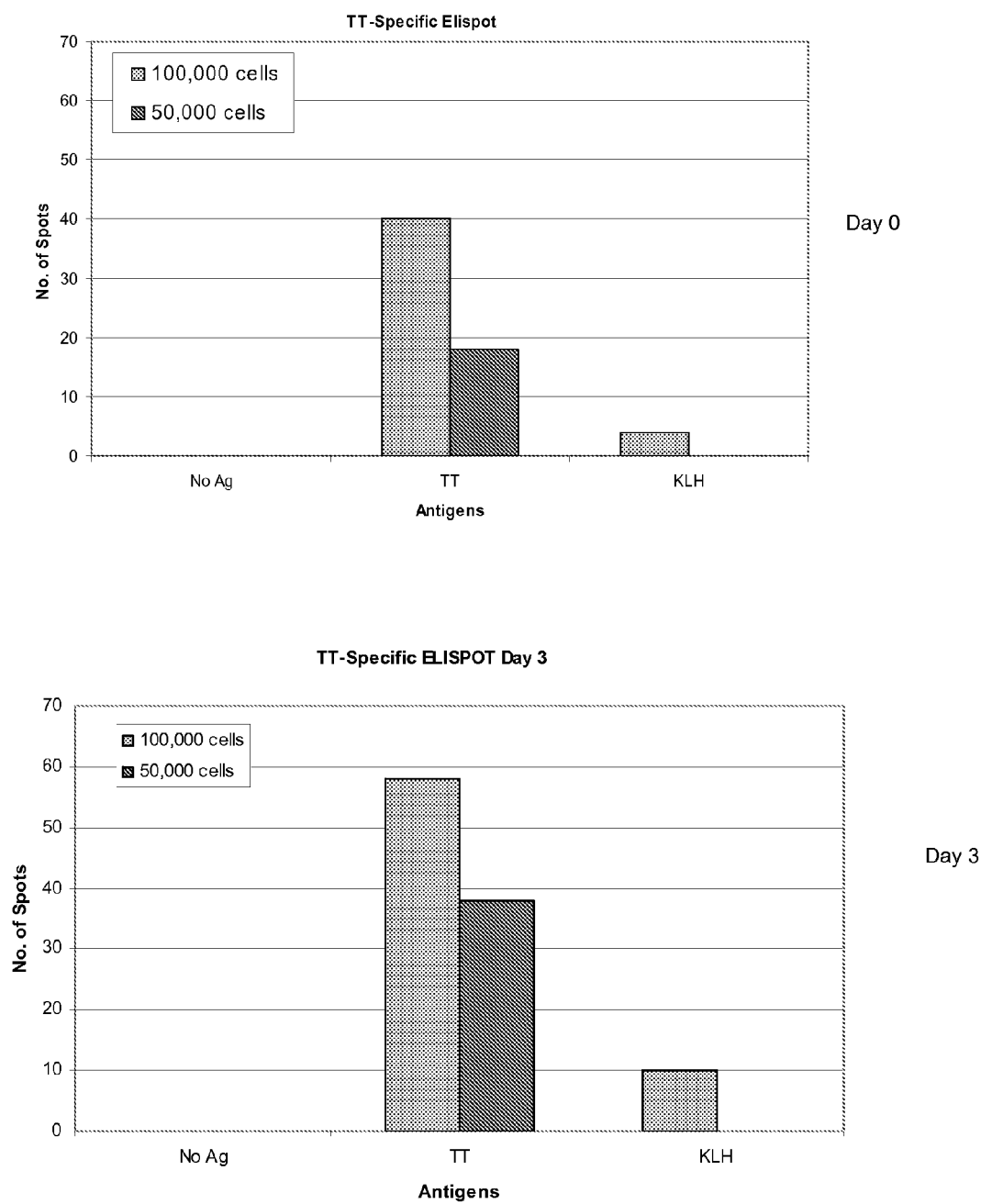
FIG. 20. Timing leukocyte interactions: tetanus toxoid-specific antibody responses.
Figure 21:
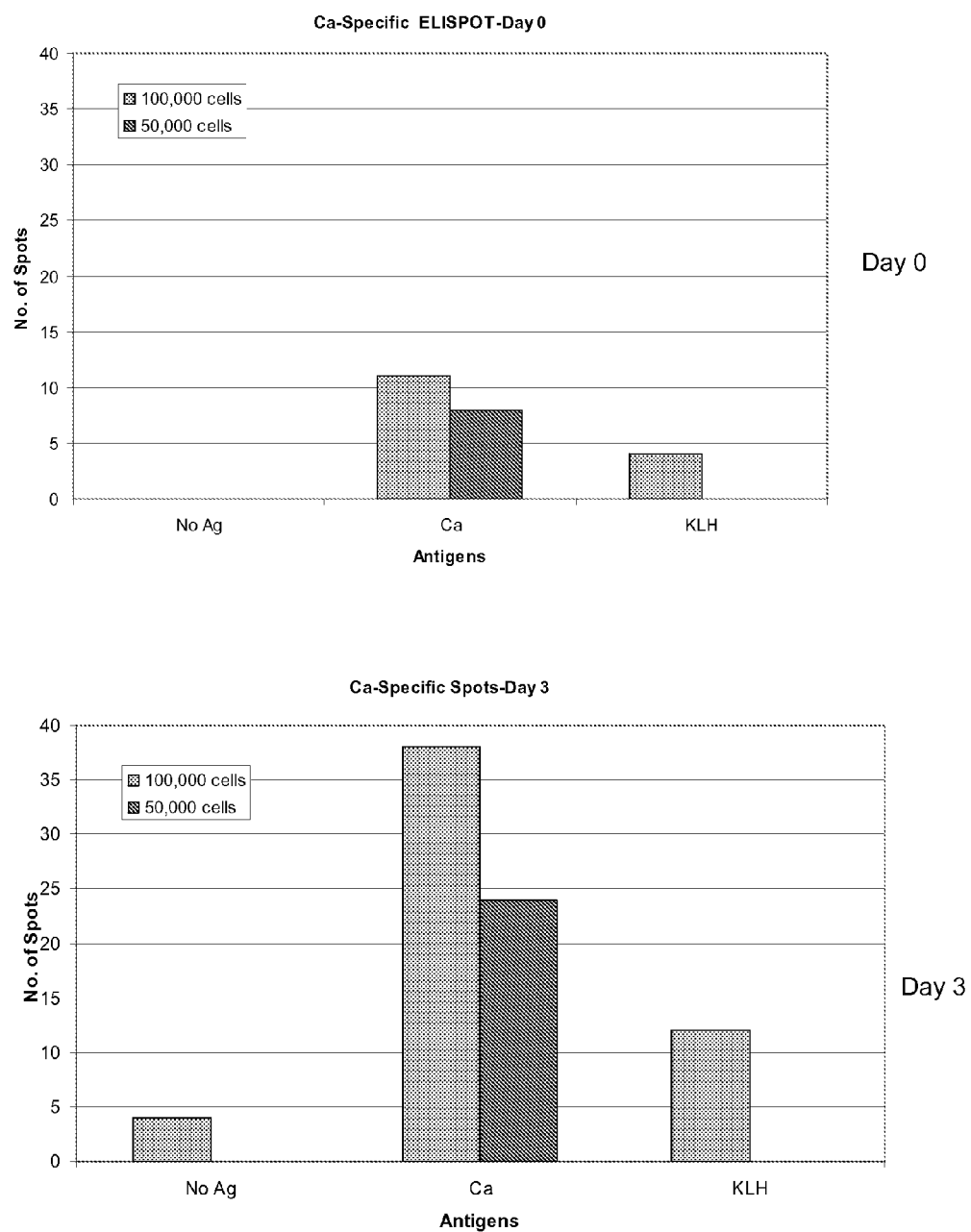
FIG. 21. Timing leukocyte interactions: *C. albicans*-specific antibody responses.

It was found that the pre-culturing of T cells with antigen-pulsed DCs and then adding B lymphocytes at day 3 of culture gave higher proliferative responses (FIG. 18) and a greater number of antigen-specific antibody responses, as indicated by the ELISPOT data in response to both soluble TT and Ca antigen, as compared to having B cells added at day 0 of culture (FIG. 19). The anti-TT titer from the donor serum was only ~3 µg/ml. The result suggests that a limiting factor in inducing recall response using donors with low antibody levels is the lack of functioning helper T cells. This may also be the case for weak naïve immune responses. As such, the present invention's process of timing leukocyte interactions provides a strategy to enhance in vitro immune responses. We have shown that two- and three-way interactions of the dendritic cells, B cells, and T cells, in a defined sequential order of events are important (i.e., that the timing of immunological events leads to stronger immune responses).

Under physiological conditions within lymph nodes, the generation of antigen-specific T cells by DCs in the paracortex usually occurs before the induction of specific B cell responses in the cortex. Embodiments of the present invention mimic this sequence of events. Co-cultures were established in which B cells were added to DC/T cell cultures at days 0 and 3, and the induction of specific responses were evaluated at days 7 and 10, respectively. The results of this experiment provide evidence that the delayed addition of autologous B cells to T/DC co-cultures triggered a marked enhancement of antigen-specific T and B cell proliferation (data not shown) and a 2-3-fold increase in the number of antigen-specific B cells against TT and a whole protein preparation from *C. albicans*.

Example 7

Enhanced Influenza-Specific IgG Response in Co-Cultures with Delayed Addition of B Cells A similar enhancement of influenza-specific T and B cell responses was observed when DCs and T cells were cocultured for 1 day prior to the addition of B cells. In this case, as well, the B cells were pre-pulsed with either Fluzone or HK A/NC for 24 h prior to being introduced to the DC/T cell cocultures. We have found that the response of T cells to antigen-loaded DCs may be hampered by the presence of B cells (data not shown); it is possible that these weak APCs out-compete the small number of DCs (B cells outnumber DCs by ~30 to 1 under the experimental conditions of this example) for access to the T cells. The 1-3 day delay in adding B cells to the cultures may provide sufficient time for the DCs to initiate the activation/differentiation of memory antigen-specific T cells.

Figure 22:
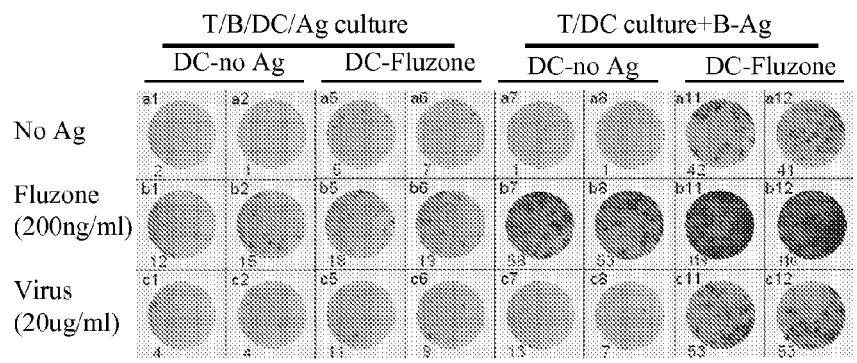
FIG. 22. Enhanced specific IgG response in co-cultures with delayed addition of B cells prepulsed with antigen.
Figure 22:
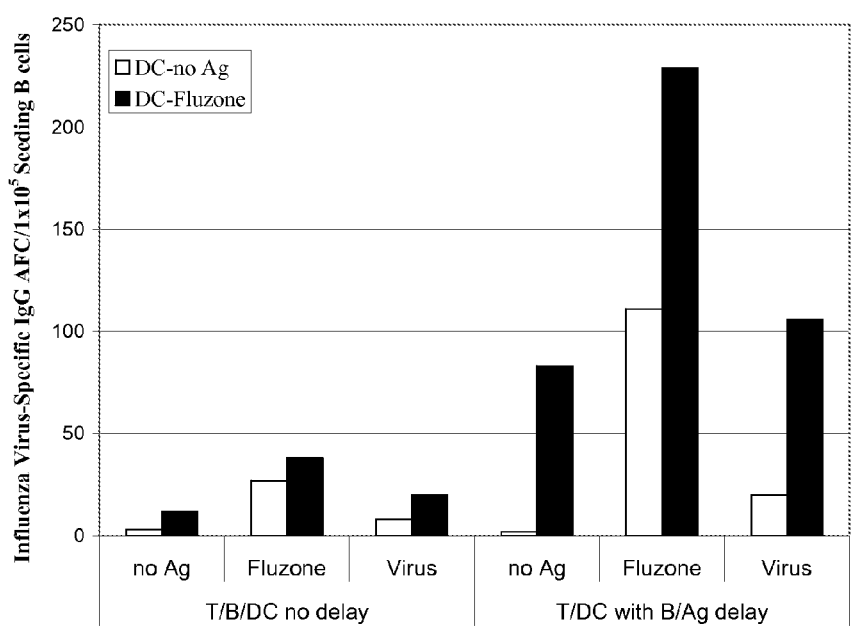

Co-culture was performed. Briefly, CD14+ monocytes sorted from PBMCs were cultured in X-Vivo medium containing GM-CSF and IL-4. At day 5 of culture, DCs were pulsed with antigen, followed by addition of maturation factor TNFα 24 h later. Then, the cells were incubated for another 24 h, harvested, and used as APCs in co-cultures. T and B cells were sorted from PBMCs, using the Miltenyi negative selective method. In some cultures, T and B cells, DCs and, antigen were added together into the wells (T/B/DC, no delay). In other conditions, T cells and DCs were cultured together. B cells were then pulsed with antigen in separate wells overnight. Then, the antigen-containing medium was removed from the B cell wells and the B cells were added into corresponding T/DC wells. Elispot assays were performed at day 7 of culture (FIG. 22). The influenza virus used in this example was the inactivated New Caledonia strain.

Example 8

B Cells Pulsed with Antigen, which were then Added One Day Later to a T/DC Culture Produced a Stronger Response than T/B/DC/Antigen Co-Culture The T/DC+B-antigen culture protocol may enhance B cell survival and the B cell response (see examples with Fluzone- and influenza virus-triggered cultures). We sought to compare B cell responses in two different culture conditions. The first was T and B cells and DCs cultured together, with or without antigen (Ag). The other was to culture Ag-pulsed DCs with T cells first, in the absence of Ag. Simultaneously, B cells were pulsed with antigen separately. After one day of prepulsing the B cells with antigen, the Ag was removed and the prepulsed B cells were added to the T cell+DC cultures (T/DC+B-Ag system). We also sought to compare the effect of DCs matured with TNFα or anti-CD40.

Example 9

Comparison of the Sensitivity of Three Different Methods to Obtain Antigen-Specific B Cell Responses to the DTaP Vaccine The serum TT titer is of the blood donor was ~98 µg/mL. The culture condition: ~2.5×10$^5$ T cells and ~2.5×10$^5$ B cells were cultured with DTaP-pulsed DCs (1:100 dilution of vaccine) in three different ways:

Method 1: T and B cells and DCs were cultured together with additional antigen (1:200 dilution of DTaP vaccine) all at the same time, Method 2: DTaP-pulsed DCs and T cells were cultured together for one day and then freshly purified B cells and additional DTaP vaccine (1:200 dilution) were added to the culture after 24 h, Method 3: DTaP-pulsed DCs and T cells were cultured together and simultaneously, B cells were pulsed with DTaP vaccine (1:200 dilution) in separate wells. After one day, the antigen-pulsed B cells were added to T cell/DC culture wells.

Figure 23:
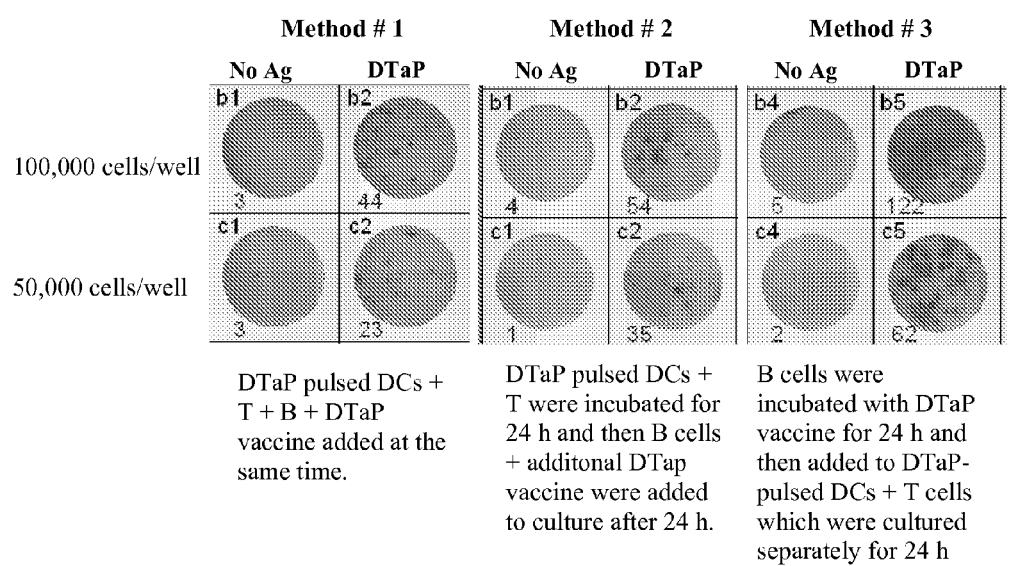
FIG. 23. Comparative analysis of three methods of sequential timing for DTaP-specific ELISPOT responses.
Figure 24:
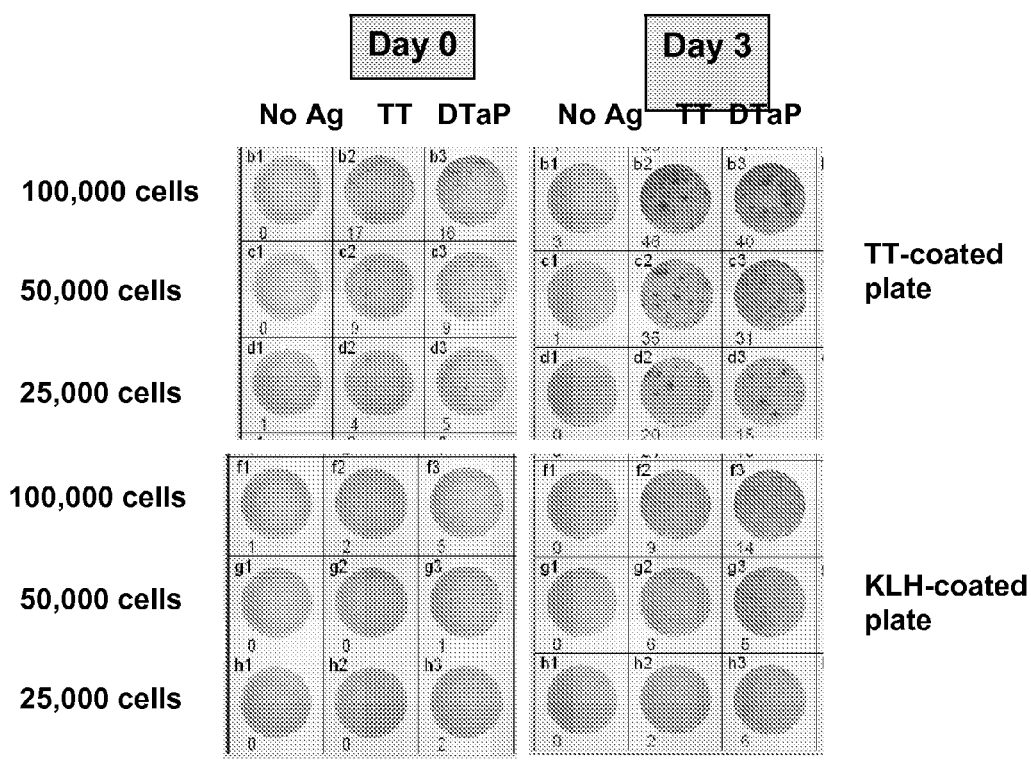
FIG. 24. TT- and DTaP-specific ELISPOT responses.

As shown in FIG. 23, method 3 was more sensitive, in terms of antigen-specific antibody responses.

Example 10

Kinetics of antigenic-specific T and B cell responses to soluble-TT and DTaP, examined by adding B cells at days 0 or 3 of the assay. The serum TT titer of the blood donor was ~35 µg/mL. In this example, ~1.5×10$^6$ monocytes were cultured in ~5 mL X-Vivo medium, supplemented with IL-4 (~25 ng/mL) and GM-CSF (~100 ng/mL) to make immature DCs. Six days later, ~25 ng/mL of TNF-α+~1 µg/mL TT antigen or ~1:100 dilution of DTaP vaccine were added to each well to provide antigen for processing and TNF-α for DC maturation. On day 7, DCs were isolated, centrifuged, and washed with medium. Then, ~2.5×10$^5$ CD4 T cells/well was cultured for 0 and 3 days with TT-pulsed DCs (~1:60) or DTaP-pulsed DCs, to present TT-Ag or DTaP-Ag, and to prime the T cells. Next, ~2.5×10$^5$ B cells/well were added to the in vitro TT- or DTaP-primed T cells+DCs culture at day 0 or day 3 after setting up the assay. Additional, TT-Ag (~100 ng/mL) or DTaP-Ag (~1:200 dilution) was also added to the culture to stimulate antigen-specific B cells. Seven days after addition of the B cells, cells were isolated to analyze the TT- or DTaP-specific proliferative response, using a flow cytometer, and TT- or DTaP-specific antibody responses, using an ELISpot assay. The assay was read on day 7 for controls (day 0) and then again at day 10 (day 3; 7 days after the addition of B cells at day 3).

Figure 25:
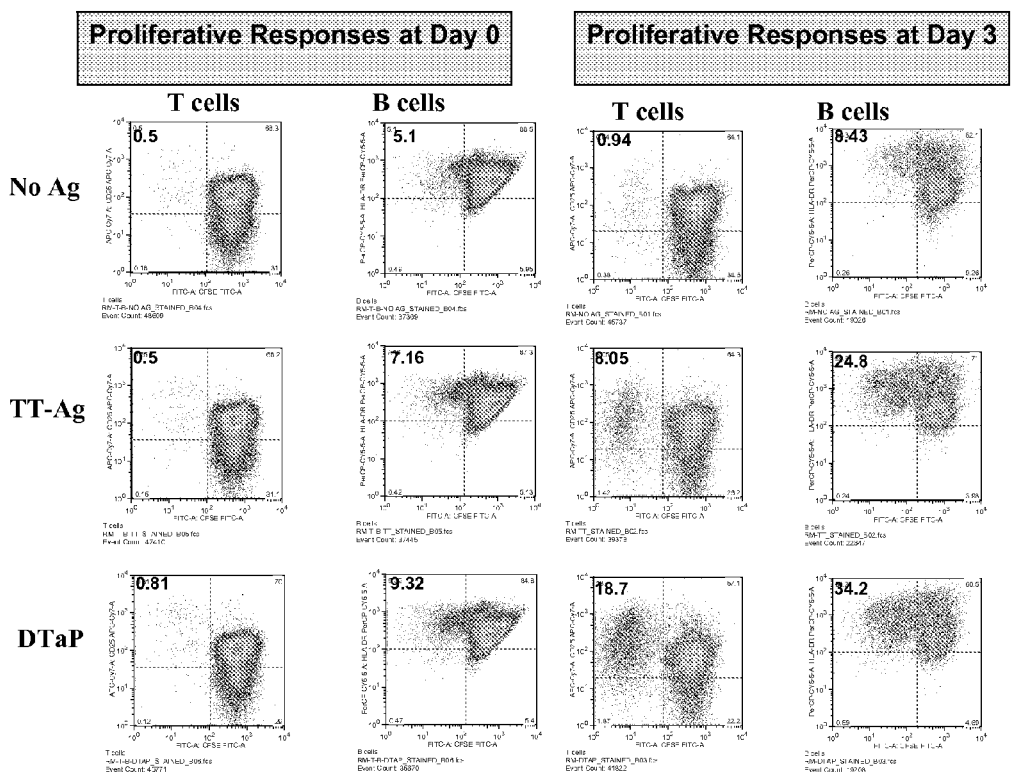
FIG. 25. Delayed addition of B cells significantly increased antigen-specific T and B cell proliferative responses.
Figure 26:
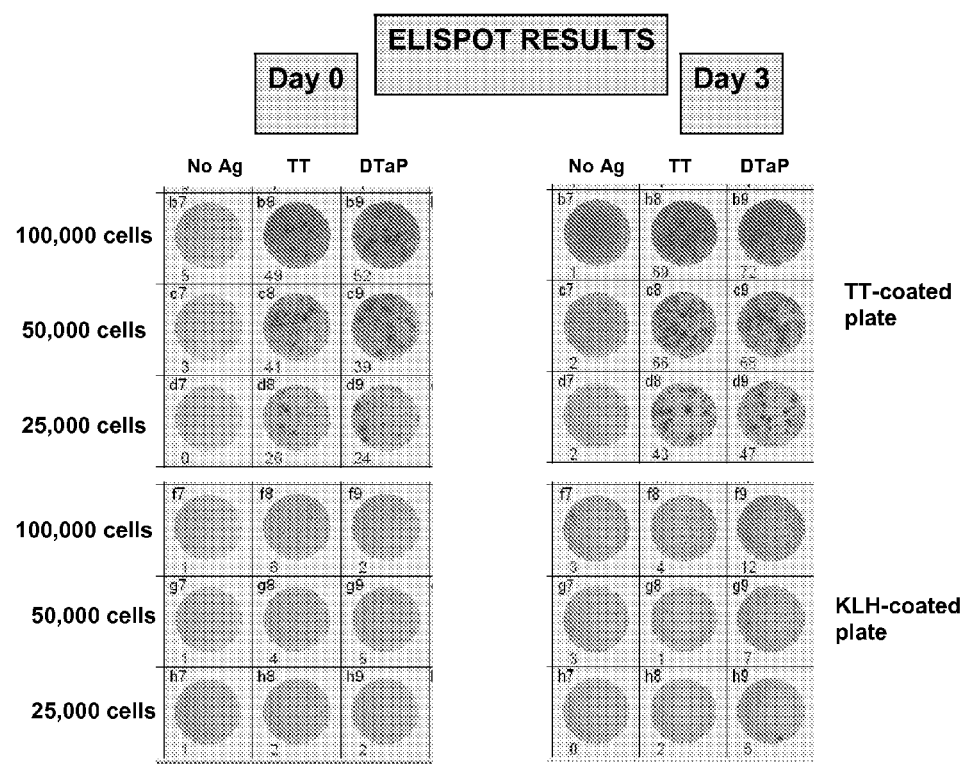
FIG. 26. Delayed addition of B cells significantly increased B cell responses.
Figure 27:
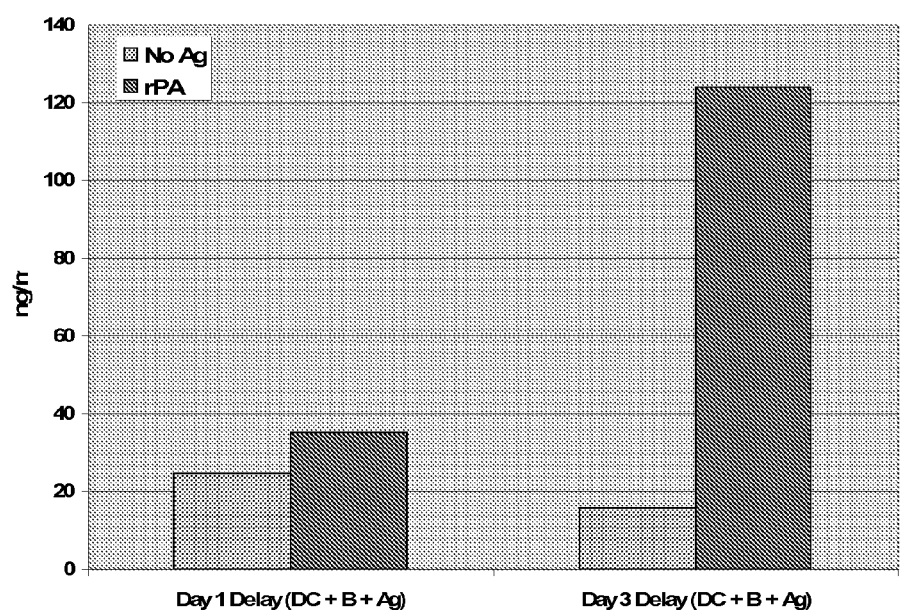
FIG. 27. Kinetics of antigen-pulsed DC and B cell interaction (day 3 versus day 1) on B cell responses to naïve antigens (rPA) in collagen/Transwell lymphoid tissue equivalent: ELISA results.

As shown in FIG. 25, delayed addition of B cells, at day 3 in this example, significantly increased antigen-specific T and B cell proliferative responses. As shown in FIG. 26, delayed addition of B cells, at day 3 in this example, significantly increased B cell responses.

Example 11

A human immune model system is prepared, comprising an irradiated mouse, wherein the irradiated mouse comprises: a) radiation-resistant follicular dendritic cells (FDCs); b) a population of human PBLs; and, c) antigen/antibody immune complexes, wherein the mouse is immunocompetent before irradiation. This method for producing this human immune model system comprises a) in vitro culturing human T cells with antigen-pulsed dendritic cells (DC) for sufficient time to produce primed CD4+ helper T cells in a T cell/DC culture to produce a T/DC population; b) combining antigen-pulsed human B cells with the in vitro T cell/DC population of part a) to produce a B/T/DC population; c) inserting the B/T/DC population of part b) into the lymph system of an irradiated mouse, wherein the mouse is immunocompetent before irradiation; whereby the irradiated mouse comprising the B/T/DC population is a human immune model system.

Human antibodies are produced by a method comprising collecting the antibodies produced by the human immune model system, described, wherein the antibodies are polyclonal antibodies. Additionally, human antibodies are produced by a) immortalizing B cells obtained from the human immune model system to produce hybridomas, b) cloning each hybridoma; c), culturing each hybridoma to produce monoclonal antibodies; and, collecting the monoclonal antibodies.

Example 12

Kinetics of Antigen-Pulsed DC and B Cell Interaction (Day 3 versus Day 1) on B Cell Responses to Naïve Antigens (rPA) in Collagen/Transwell Lymphoid Tissue Equivalent DC preparation. ~5×10$^6$ monocytes, positively isolated from PBMCs, were cultured in 5 ml X-Vivo media supplemented with IL-4 (~25 ng/mL) and GM-CSF (~100 ng/mL) to make immature DCs. Additional IL-4 and GM-CSF were added at day 3 of the culture. DC maturation and antigen pulsing. At day 6, DCs were pulsed with rPA antigen (~2 µg/mL) or gp120 (~1 µg/mL) for ~5-6 h and matured overnight with TNF-α (~25 ng/mL) and cells were harvested at day 7 to set up the experiment.

Addition time sequence and assay set-up. A total of ~5 million lymphocytes per well was used.

Experimental Plan: T:B cell ratio=~1:2 and DC:lymphocyte ratio: ~1:40

| | DC + T (day 1)<br>DC + B + Ag (day 1) | DC + T (day 3)<br>DC + B + Ag (day 3) |
|---|---|---|
| no Ag | | |
| rPA | | |

Duplicate wells were used for each condition. On the day of the experimental set-up, ~1.7 million CD4$^+$ T cells were cultured with antigen-pulsed DCs (~1:40) in 48-well plates for either day 1 or day 3. Similarly, naïve B cells were cultured with antigen-pulsed DCs (~1:40) with additional soluble antigen (rPA-Ag (1 μg/mL) for either day 1 or day 3 in separate 48-wells plates.

After day 1 or 3, both DC+CD4+ T and DC+naïve B cells were mixed together and spun down: the supernatant was collected and saved. The cell pellet was resuspended in ~33 μL of X-VIVO media, containing rPA-Ag (3× of ~1 μg/mL) and chemokines (3× of ~1 μg/mL each of CCL21 and CXCL13). Then, ~70 μL neutralized collagen (~1.9 mL of ~3 mg/mL collagen+~100 μL 10×PBS+~20 μL 1 M NaOH and ~8 μL of fibronectin (~5 mg/mL); the pH was checked (~7.2 to 7.4)) was mixed and poured into a Transwell device. The plate was incubated at ~37° C. for ~30-40 min to cast the collagen.

The final concentration of antigen and chemokines in the collagen cushion was ~1 μg/mL. After the collagen had congealed, ~600 μL of pre-warmed X-VIVO media, containing 1×rPA antigen was added to the bottom chamber of the Transwell and supernatant collected from the overnight cultured cells (~300 μL) was added on the top of the collagen cushion.

Media changes and harvesting. At days 7 and 14 of the culture, ~600 μL of pre-warmed antigen-containing media (rPA, ~0.5 μg/mL) was changed in the bottom chamber of the Transwell. At day 21, cells were harvested by adding ~100 μL collagenase solution (~20 μL of stock collagenase (Sigma)+ ~80 μL of X-VIVO media} on the top of the collagen. The plate was incubated for ~30 min at 37° C. The cells were then resuspended, mixed, and added into ~5 mL X-VIVO media for washing. The cells were washed ~2-3 times with X-VIVO media, counted by the trypan blue exclusion method, and incubated with IL-21 cytokine.

Post-harvest IL-21 stimulation. Cells were harvested at day 21 and stimulated with IL-21 alone (~20 ng/mL) for ~3 days in 48-well tissue culture plates. Typically, ~2.5 million cells per wells were added with IL-21 in ~500 μL media. After ~3 days, cells were washed three times in the tube, counted, and used for ELISPOT analysis (~$10^5$ cells per well).

Result. In an ELISA, a ~4-fold increase in rPA-specific IgM antibodies was detected when antigen-loaded DCs were cultured with B cells in the presence of antigen (rPA, ~1 μg/mL) for 3 days, as compared to day 1. Antigen-pulsed DCs and T cells were also added at days 3 and 1, respectively.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An in vitro method of enhancing antigen-induced responsiveness of B cells in a population comprising:
   a) prepulsing a population of dendritic cells (DCs) with a selected antigen to obtain an antigen-prepulsed DC population;
   b) culturing the antigen-prepulsed DC population of a) with a population of T cells to obtain a T/DC/Ag cell population;
   c) prepulsing a population of B cells with the selected antigen followed by removal of the antigen to obtain an antigen-prepulsed B cell population (B-Ag); and
   d) co-culturing the T/DC/Ag cell population of b) with the B-Ag cell population of c), after at least about 24 hours of culturing in b), to obtain a T/DC+B-Ag co-culture under conditions permitting a B cell response; wherein the number of B cells producing antibody in the T/DC+B-Ag co-culture is greater than the number of B cells producing antibody in a co-culture in which the T cells were co-cultured with an antigen-prepulsed DC population for less than 24 hours prior to addition of antigen-prepulsed B cells; thereby enhancing antigen-induced responsiveness of B cells in a population.

2. The method of claim 1, wherein the culturing of b) is for about three days.

3. An in vitro method of enhancing antigen-induced responsiveness of B cells in a population comprising:
   a) prepulsing a population of dendritic cells (DCs) with a selected antigen to obtain a first antigen-prepulsed DC population;
   b) culturing the first antigen-prepulsed DC population of a) with a population of T cells to obtain a T/DC/Ag cell population;
   c) prepulsing a second population of DCs with the selected antigen to obtain a second antigen-prepulsed DC population;
   d) culturing the second antigen-prepulsed DC population of c) with a population of B cells to obtain a B cell-dendritic cell population (B-DC);
   e) co-culturing the T/DC/Ag cell population of b) with the B-DC cell population of d) after at least about 24 hours of culturing in b), to obtain a T/DC+B-DC co-culture under conditions permitting a B cell response; wherein the number of B cells producing antibody in the T/DC+B-DC co-culture is greater than the number of B cells producing antibody in a co-culture in which the T cells were co-cultured with an antigen-prepulsed DC population for less than 24 hours prior to addition of B cell-dendritic cells; thereby enhancing antigen-induced responsiveness of B cells in a population.

4. The method of claim 3, wherein the culturing of b) is for about three days.

5. The method of claim 1, further comprising: e) separating antibody-producing B cells from the T/DC+B-Ag co-culture.

6. The method of claim 3, further comprising: e) separating antibody-producing B cells from the T/DC+B-DC co-culture.

* * * * *

UNITED STATES PATENT AND TRADEMARK OFFICE
CERTIFICATE OF CORRECTION

| | | |
|---|---|---|
| PATENT NO. | : 7,709,257 B2 | Page 1 of 1 |
| APPLICATION NO. | : 11/819335 | |
| DATED | : May 4, 2010 | |
| INVENTOR(S) | : John G. Tew et al. | |

It is certified that error appears in the above-identified patent and that said Letters Patent is hereby corrected as shown below:

Column 1, at line 2 insert:

--STATEMENT REGARDING FEDERALLY SPONSORED RESEARCH

This invention was made with government support under contract number NBCHC060058, awarded by the Defense Advanced Research Projects Agency, issued by the U.S. Army Medical Research Acquisition Activity, and administered by the U.S. Department of the Interior-National Business Center. The government has certain rights in the invention.--

Signed and Sealed this

Seventeenth Day of August, 2010

David J. Kappos
*Director of the United States Patent and Trademark Office*